(12) United States Patent
Newman et al.

(10) Patent No.: US 7,402,434 B2
(45) Date of Patent: Jul. 22, 2008

(54) SPLICE CHOICE ANTAGONISTS AS THERAPEUTIC AGENTS

(76) Inventors: Stuart A. Newman, 23 Iroquois Rd., Pleasantville, NY (US) 10570; Natalie B. Bronstein, 78 Morningside Dr., Patterson, NY (US) 12563

( * ) Notice: Subject to any disclaimer, the term of this patent is extended or adjusted under 35 U.S.C. 154(b) by 0 days.

(21) Appl. No.: 09/849,967

(22) Filed: May 8, 2001

(65) Prior Publication Data

US 2002/0068321 A1 Jun. 6, 2002

Related U.S. Application Data

(60) Provisional application No. 60/202,657, filed on May 8, 2000.

(51) Int. Cl.
*C12N 15/87* (2006.01)

(52) U.S. Cl. .......................... 435/455; 514/44

(58) Field of Classification Search .............. 514/44; 435/6, 375, 455
See application file for complete search history.

(56) References Cited

OTHER PUBLICATIONS

Blanchette et al (Apr. 1, 1999, The EMBO Journal, vol. 18, pp. 1939-1952).*
McNally et al (Mar. 1999, Journal of Virology, vol. 73, pp. 2385-2393).*
Caceres et al (1998, Genes Dev., vol. 12, pp. 55-66).*
Ross et al (1997, Molecular And Cellular Biology, vol. 17, pp. 2158-2165).*
Muro et al (Mol Cell Biol. Apr. 1999;19(4):2657-71).*
Hastings et al (J Biol Chem. Apr. 14, 2000;275(15):11507-13).*
Maniatis and Tasic (2002, Nature, vol. 236, pp. 236-243).*
Caputi et al., (1999, The EMBO Journal, vol. 18, pp. 4060-4067).*
Purcell and Martin (J. Virol.,1993, vol. 67, pp. 6365-6378).*
Damgaard et al., (2002, RNA, vol. 8, pp. 1401-1415).*
Section 2. Virology (total 5 pages) of Medical Microbiology (S. Baron, ed) downloaded from url>>cbi.nlm.nih.gov/books on Apr. 20, 2004.*
Lee et al., (Faseb J., 2000, vol. 14, pp. 516-522 abstract only).*
Voet et al (Biochemistry, 1990, John Wiley & Sons, p. 856 only).*
Sambrook et al (1989, Molecular Cloning, A Laboratory Manuel, 2nd Edition, pp. 16.30-16.33).*

* cited by examiner

*Primary Examiner*—Misook Yu
(74) *Attorney, Agent, or Firm*—Kelley Drye & Warren LLP

(57) ABSTRACT

The invention relates to methods and reagents for influencing alternative RNA splicing in living cells. More particularly, the invention relates to novel means for influencing RNA splice choice in living cells using polynucleotide-based reagents that compete for binding sites in nucleotide binding proteins, and novel methods for using these reagents as therapeutics.

25 Claims, 4 Drawing Sheets

```
   1 gcgtctccac ccctcagcgg gcggcggtga gtgcgccagg ccagcgccgg cgtgggaccg
  61 agcgggcgtg aaggcgcgag ctgaacgctg gcacggtttc ctagatctaa aagaaaggcc
 121 gagttagagt acccttccaa AATGCTGCT ATTAAGGAAG AGAGAGAGGT GGAAGATTAC
 181 AAGAGAAAAA GGAAGACGAT CAGCACAGGC CATGAGCCTA AGGAGCCAGA GCAGTTGAGA
 241 AAGCTGTTCA TTGGAGGTCT GAGCTTCGAG ACGACGGATG ATAGCTTGAG AGAGCACTTT
 301 GAAAAATGGG GCACACTCAC GGACTGTGTG GTGATGAGAG ACCCACAAAC AAAACGTTCC
 361 AGAGGCTTTG GCTTTGTTAC TTACTCTTGC GTGGAAGAGG TGGATGCGGC CATGAGCGCT
 421 CGACCACATA AGGTGGATGG ACGTGTGGTT GAACCAAAGA GAGCAGTTTC AAGGGAGGAT
 481 TCTGTAAAGC CTGGGGCGCA CTCTCACAGTA AAGAAAATAT TTGTTGGTGG CATTAAAGAA
 541 GATACAGAAG AATATAATTT AAGGGGGTAC TTTGAAACAT ATGCAAGAT CGAAACGATA
 601 GAAGTCATGG AAGACAGACA AAGTGGAAAG AAAAGAGGCT TCGCTTTTGT AACTTTTGAT
 661 GATCACGATA CAGTTGATAA AATTGTTGTT CAGAAATAGC ATACTATAAA TGGTCATAAC
 721 TGCGAAGATA AAAAGCACT CTCAAAACAA GAGATGCAGA CTGCCAGCTC TCAGAGAGGT
 781 CGTGGGGGTG GTTCAGGCAA CTTCATGGGT CGTGGAAATT TTGGAGGTGG TGGAGGAAAC
 841 TTTGGCCGAG GAGGAAACTT TGGTGAAGA GGAGGCTATG GGGGTGGTGG TGGCGGTGGT
 901 GGGAGCAGAG GAAGCTTTGG GGGTGGTGAT GGATACAACG GATTTGGTGA TGGTGGCAAC
 961 TATGGAGGTG GTCCTGGCTA TGGCAGCAGA GGGGGTTATG GTGGTGGTGG AGGACCAGGA
1021 TATGGAAACC CAGGTGGTGG ATATGGAGGT GGAGGAGGAG GATATGGTGG CTACAATGAA
1081 GGAGGCAATT TTGGAGGTGG TAATTATGGA GGCAGTGGAA ACTACAATGA CTTTGGTAAC
1141 TACAGTGGAC AGCAGCAGTC CAATTACGGT CCCATGAAAG GTGGTGGCAG TTTTGGTGGT
1201 AGAAGTTCAG GCAGTCCCTA TGGTGGTGGT TATGGATCTG GAAGTGAAG TGGGGGCTAT
1261 GGTGGTAGAA GATTCTaaaa atgctaccag aaaaaggct acagttctta gcaggagaga
1321 gagcgaggag ttgtcaggaa agctgcaggt tactttgaga cagtcgtccc aaatgcatta
1381 gaggaactgt aaaatctgcc acagaaggaa cgatgatcca tagtcagaaa agttactgca
1441 gcttaaacag gaaacccttc ttgttcagga ctgtcatagc cacagtttgc aaaaagagca
1501 gctattggtt aatgcaatgt agtgtcgtta gatgtacatc ctgaggtctt tatctgttgt
1561 agctttgtct ttctttttc ttttattt cccattacat caggtatatt gccctgtaaa
1621 ttgtggtagt ggtaccagga ataaacaaat taaggaattt ttggcttttc aaaaaaaaaa
1681 aaaaaaaaa
```

Fig. 1a

```
CHKA1  - MAAIKEEREVEDYKRKRKTISTGHEPKEPEQLRKLFIGGLSFETTDDSLR   -50
         |                     |  ||||||||||||||||||| |||
HUMA1  - M---------------------SKSESPKEPEQLRKLFIGGLSFETTDESLR -31

CHKA1  - EQFEKWGTLTDCVVMRDPQTKRSRGFGFVTYSCVEEVDAAMSARPHKVDG  -100
         || ||||||||||||| |||||| ||||||||| |||||||| ||||||||
HUMA1  - SHFEQWGTLTDCVVMRDPNTKRSRGFGFVTYATVEEVDAAMNARPHKVDG  -81

CHKA1  - RVVEPKRAVSREDSVKPGAHLTVKKIFVGGIKEDTEEYNLRGYFETYGKI  -150
         |||||||||||||| |||||||||||||||||||||  || |||  ||||
HUMA1  - RVVEPKRAVSREDSQRPGAHLTVKKIFVGGIKEDTEEHHLRDYFEQYGKI  -131

CHKA1  - ETIEVMEDRQSGKKRGFAFVTFDDHDTVDKIVVQKYHTINGHNCEDKKAL  -200
         | || | || |||||||||||||||| ||||| |||||| |||||| |||
HUMA1  - EVIEIMTDRGSGKKRGFAFVTFDDHDSVDKIVIQKYHTVNGHNCEVRKAL  -181

CHKA1  - SKQEMQTASS-QRGRGGGSGNFMGRGNFGGGGG-------NFGRGGNFGG  -242
         |||||  ||| |||| |||       ||||||||        ||||||||
HUMA1  - SKQEMASASSSQRGRSGS-------GNFGGGRGGGFGGNDNFGRGGNFSG  -224

CHKA1  - RGGYGGGGGGGSRGSFGGGDGYNGFGDGGNYGGGPGYGSRGGYGGGGGP  -292
         |||  ||   | ||||  |||||||||                       
HUMA1  - RGGFGGSRGGGGYGGS---GDGYNGFGNDGS--------------------  -252

CHKA1  - GYGNPGGYGGGGGGYGGYNEGGNFGGGNYGGSGNYNDFGNYSGQQQSNY  -342
                              || | ||||||| |  ||
HUMA1  - ---------------------------NFGGGGSYNDFGNYNNQS-SNF  -273

CHKA1  - GPMKGGGSFGGRSSGSPYGGG-------------YGSGSGSGGYG-GRRF  -378
         |||||||  ||||||| |||||             || | || ||||
HUMA1  - GPMKGG-NFGGRSSG-PYGGGQYFAKPRNQGGYGGSSSSSYGSGRRF   -320
```

Fig. 1b

SPLICE CHOICE ANTAGONISTS AS THERAPEUTIC AGENTS

CROSS REFERENCE TO RELATED PATENT APPLICATIONS

This application is related to and claims priority on U.S. provisional patent application Ser. No. 60/202,657 filed May 8, 2000.

GOVERNMENT SUPPORT

This work was supported by a grant from the National Institutes of Health (1 R03 HD37194: Spatiotemporal regulation of fibronectin).

FIELD OF THE INVENTION

The invention relates to methods and reagents for influencing alternative RNA splicing in living cells. More particularly, the invention relates to novel means for influencing RNA splice choice in living cells using polynucleotide-based reagents that compete for binding sites in nucleotide binding proteins, and novel methods for using these reagents as therapeutics.

REFERENCES CITED

Adam, S. A., Nakagawa, T., Swanson, M. S., Woodruff, T. K., and Dreyfuss, G. (1986). mRNA polyadenylate-binding protein: gene isolation and sequencing and identification of a ribonucleoprotein consensus sequence. *Mol Cell Biol* 6, 2932-43.

Aitchison, J. D., Blobel, G., and Rout, M. P. (1996). Kap104p: a karyopherin involved in the nuclear transport of messenger RNA binding proteins. *Science* 274, 624-7.

Akamatsu, W., Okano, H. J., Osumi, N., Inoue, T., Nakamura, S., Sakakibara, S., Miura, M., Matsuo, N., Darnell, R. B., and Okano, H. (1999). Mammalian ELAV-like neuronal RNA-binding proteins HuB and HuC promote neuronal development in both the central and the peripheral nervous systems. *Proc Natl Acad Sci U S A* 96, 9885-90.

Alvarez, I. S., Araujo, M., and Nieto, M. A. (1998). Neural induction in whole chick embryo cultures by FGF. *Dev Biol* 199, 42-54.

Amendt, B. A., Hesslein, D., Chang, L. J., and Stoltzfus, C. M. (1994). Presence of negative and positive cis-acting RNA splicing elements within and flanking the first tat coding exon of human immunodeficiency virus type 1. *Mol Cell Biol* 14, 3960-70.

Amendt, B. A., Si, Z. H., and Stoltzfus, C. M. (1995). Presence of exon splicing silencers within human immunodeficiency virus type 1 tat exon 2 and tat-rev exon 3: evidence for inhibition mediated by cellular factors [published erratum appears in Mol Cell Biol 1995 Nov;15(11):6480]. *Mol Cell Biol* 15, 4606-15.

Amrein, H., Gorman, M., and Nothiger, R. (1988). The sex-determining gene tra-2 of Drosophila encodes a putative RNA binding protein [published erratum appears in Cell 1989 Jul 28;58(2):following 419]. *Cell* 55, 1025-35.

Anderson, P. J., Hall, C. M., Evans, R. D., Hayward, R. D., and Jones, B. M. (1999). The feet in Apert's syndrome. *J Pediatr Orthop* 19, 504-7.

Arman, E., Haffner-Krausz, R., Chen, Y., Heath, J. K., and Lonai, P. (1998). Targeted disruption of fibroblast growth factor (FGF) receptor 2 suggests a role for FGF signaling in pregastrulation mammalian development. *Proc Natl Acad Sci U S A* 95, 5082-7.

Arman, E., Haffner-Krausz, R., Gorivodsky, M., and Lonai, P. (1999). Fgfr2 is required for limb outgrowth and lung-branching morphogenesis. *Proc Natl Acad Sci U S A* 96, 11895-9.

Arrigo, S. J., and Chen, I. S. (1991). Rev is necessary for translation but not cytoplasmic accumulation of HIV-1 vif, vpr, and env/vpu 2 RNAs. *Genes Dev* 5, 808-19.

Arts, G. J., Fornerod, M., Mattaj, I. W. (1998). Identification of a nuclear export receptor for tRNA. *Current Biology* 8, 305-314.

Aviezer, D., Safran, M., and Yayon, A. (1999). Heparin differentially regulates the interaction of fibroblast growth factor-4 with FGF receptors 1 and 2. *Biochem Biophys Res Commun* 263, 621-6.

Baba-Aissa, F., Van den Bosch, L., Wuytack, F., Raeymaekers, L., and Casteels, R. (1998). Regulation of the sarco/endoplasmic reticulum Ca(2+)-ATPase (SERCA) 2 gene transcript in neuronal cells. *Brain Res Mol Brain Res* 55, 92-100.

Balinsky, B. I. (1970). "An Introduction to Embryology." W. B. Saunders, Philadelphia.

Bandziulis, R. J., Swanson, M. S., and Dreyfuss, G. (1989). RNA-binding proteins as developmental regulators. *Genes Dev* 3, 431-7.

Bell, L. R., Horabin, J. I., Schedl, P., and Cline, T. W. (1991). Positive autoregulation of sex-lethal by alternative splicing maintains the female determined state in Drosophila. *Cell* 65, 229-39.

Beyer, A. L., Christensen, M. E., Walker, B. W., and LeStourgeon, W. M. (1977). Identification and characterization of the packaging proteins of core 40S hnRNP particles. *Cell* 11, 127-38.

Biamonti, G., Buvoli, M., Bassi, M. T., Morandi, C., Cobianchi, F., and Riva, S. (1989). Isolation of an active gene encoding human hnRNP protein A1. Evidence for alternative splicing. *J Mol Biol* 207, 491-503.

Bischoff, F. R., and Gorlich, D. (1997). RanBP1 is crucial for the release of RanGTP from importin beta-related nuclear transport factors. *FEBS Lett* 419, 249-54.

Blanchette, M., and Chabot, B. (1997). A highly stable duplex structure sequesters the 5' splice site region of hnRNP A1 alternative exon 7B. *Rna* 3, 405-19.

Boche, I., and Fanning, E. (1997). Nucleocytoplasmic recycling of the nuclear localization signal receptor alpha subunit in vivo is dependent on a nuclear export signal, energy, and RCC1. *J Cell Biol* 139, 313-25.

Bonifaci, N., Moroianu, J., Radu, A., and Blobel, G. (1997). Karyopherin beta2 mediates nuclear import of a mRNA binding protein. *Proc Natl Acad Sci U S A* 94, 5055-60.

Borja, A. Z. M., Meijers, C., and Zeller, L. (1993). Expression of alternatively spliced bRGR first coding exons and antisense mRNAs during chicken embryogenesis. *Developmental Biology* 157, 110-118.

Brand, B., Christ, B., and Jacob, H. J. (1985). An experimental analysis of the developmental capacities of distal parts of avian leg buds. *Am. J. Anat.* 173, 321-340.

Broad, T. E., and Ham, R. G. (1983). Growth and adipose differentiation of sheep preadipocyte fibroblasts in serum-free medium. *Eur J Biochem* 135, 33-9.

Burd, C. G., and Dreyfuss, G. (1994). RNA binding specificity of hnRNP A1: significance of hnRNP A1 high-affinity binding sites in pre-mRNA splicing. *Embo J* 13, 1197-204.

Burd, C. G., Swanson, M. S., Gorlach, M., and Dreyfuss, G. (1989). Primary structures of the heterogeneous nuclear ribonucleoprotein A2, B1, and C2 proteins: a diversity of RNA binding proteins is generated by small peptide inserts. *Proc Natl Acad Sci U S A* 86, 9788-92.

Burgess, W. H., and Maciag, T. (1989). The heparin-binding (fibroblast) growth factor family of proteins. *Annu Rev Biochem* 58, 575-606.

Burke, D., Wilkes, D., Blundell, T. L., and Malcolm, S. (1998). Fibroblast growth factor receptors: lessons from the genes. *Trends Biochem Sci* 23, 59-62.

Burrus, L. W., and Olwin, B. B. (1989). Isolation of a receptor for acidic and basic fibroblast growth factor from embryonic chick. *J Biol Chem* 264, 18647-53.

Buvoli, M., Cobianchi, F., Bestagno, M. G., Mangiarotti, A., Bassi, M. T., Biamonti, G., and Riva, S. (1990). Alternative splicing in the human gene for the core protein A1 generates another hnRNP protein. *Embo J* 9, 1229-35.

Buvoli, M., Cobianchi, F., and Riva, S. (1992). Interaction of hnRNP A1 with snRNPs and pre-mRNAs: evidence for a possible role of A1 RNA annealing activity in the first steps of spliceosome assembly. *Nucleic Acids Res* 20, 5017-25.

Caceres, J. F., Misteli, T., Screaton, G. R., Spector, D. L., and Krainer, A. R. (1997). Role of the modular domains of SR proteins in subnuclear localization and alternative splicing specificity. *J Cell Biol* 138, 225-38.

Caceres, J. F., Screaton, G. R., and Krainer, A. R. (1998). A specific subset of SR proteins shuttles continuously between the nucleus and the cytoplasm. *Genes Dev* 12, 55-66.

Caceres, J. F., Stamm, S., Helfman, D. M., and Krainer, A. R. (1994). Regulation of alternative splicing in vivo by overexpression of antagonistic splicing factors. *Science* 265, 1706-9.

Calvio, C., Neubauer, G., Mann, M., and Lamond, A. I. (1995). Identification of hnRNP P2 as TLS/FUS using electrospray mass spectrometry. *Rna* 1, 724-33.

Caputi, M., Casari, G., Guenzi, S., Tagliabue, R., Sidoli, A., Melo, C. A., and Baralle, F. E. (1994). A novel bipartite splicing enhancer modulates the differential processing of the human fibronectin EDA exon. *Nucleic Acids Res* 22, 1018-22.

Caputi, M., Mayeda, A., Krainer, A. R., and Zahler, A. M. (1999). hnRNP A/B proteins are required for inhibition of HIV-1 pre-mRNA splicing. *Embo J* 18, 4060-7.

Chabot, B. (1996). Directing alternative splicing: cast and scenarios. *Trends Genet* 12, 472-8.

Chabot, B., Blanchette, M., Lapierre, I., and La Branche, H. (1997). An intron element modulating 5' splice site selection in the hnRNP A1 pre-mRNA interacts with hnRNP A1. *Mol Cell Biol* 17, 1776-86.

Champion-Arnaud, P., Ronsin, C., Gilbert, E., Gesnel, M. C., Houssaint, E., and Breathnach, R. (1991). Multiple mRNAs code for proteins related to the BEK fibroblast growth factor receptor. *Oncogene* 6, 979-87.

Chan, C. T., and Thorogood, P. (1999). Pleiotropic features of syndromic craniosynostoses correlate with differential expression of fibroblast growth factor receptors 1 and 2 during human craniofacial development. *Pediatr Res* 45, 46-53.

Chung, S. Y., and Wooley, J. (1986). Set of novel, conserved proteins fold pre-messenger RNA into ribonucleosomes. *Proteins* 1, 195-210.

Cobianchi, F., Calvio, C., Stoppini, M., Buvoli, M., and Riva, S. (1993). Phosphorylation of human hnRNP protein A1 abrogates in vitro strand annealing activity. *Nucleic Acids Res* 21, 949-55.

Cobianchi, F., Karpel, R. L., Williams, K. R., Notario, V., and Wilson, S. H. (1988). Mammalian heterogeneous nuclear ribonucleoprotein complex protein A1. Large-scale overproduction in *Escherichia coli* and cooperative binding to single-stranded nucleic acids. *J Biol Chem* 263, 1063-71.

Cobianchi, S. F., Biamonti, G., Bassi, M. T., Buvoli, M., and Riva, S. (1990). In "The Eukaryotic Nucleus: Structure and Function" (P. a. W. Strauss, S., Ed.), Vol. Two, pp. 561, Caldwell, N.J.

Cochrane, A. W., Jones, K. S., Beidas, S., Dillon, P. J., Skalka, A. M., and Rosen, C. A. (1991). Identification and characterization of intragenic sequences which repress human immunodeficiency virus structural gene expression. *J Virol* 65, 5305-13.

Cohn, M. J., Izpisua-Belmonte, J. C., Abud, H., Heath, J. K., and Tickle, C. (1995). Fibroblast growth factors induce additional limb development from the flank of chick embryos. *Cell* 80, 739-746.

Crossley, P. H., Martinez, S., and Martin, G. R. (1996). Midbrain development induced by FGF8 in the chick embryo. *Nature* 380, 66-8.

Crozat, A., Aman, P., Mandahl, N., and Ron, D. (1993). Fusion of CHOP to a novel RNA-binding protein in human myxoid liposarcoma. *Nature* 363, 640-4.

Dahlberg, J. E., and Lund, E. (1998). Functions of the GTPase Ran in RNA export from the nucleus. *Curr Opin Cell Biol* 10, 400-8.

De Moerlooze, L., Spencer-Dene, B., Revest, J., Hajihosseini, M., Rosewell, I., and Dickson, C. (2000). An important role for the IIIb isoform of fibroblast growth factor receptor 2 (FGFR2) in mesenchymal-epithelial signalling during mouse organogenesis. *Development* 127, 483-92.

Dejgaard, K., Leffers, H., Rasmussen, H. H., Madsen, P., Kruse, T. A., Gesser, B., Nielsen, H., and Celis, J. E. (1994). Identification, molecular cloning, expression and chromosome mapping of a family of transformation upregulated hnRNP-K proteins derived by alternative splicing. *J Mol Biol* 236, 33-48.

Del Gatto, F., and Breathnach, R. (1995). A Crouzon syndrome synonymous mutation activates a 5' splice site within the IIIc exon of the FGFR2 gene. *Genomics* 27, 558-559.

Del Gatto, F., Gesnel, M. C., and Breathnach, R. (1996). The exon sequence TAGG can inhibit splicing. *Nucleic Acids Reseach* 24, 2017-2021.

Del Gatto, F., and Breathnach, R. (1995). Exon and intron sequences, respectively, repress and activate splicing of a fibroblast growth factor receptor 2 alternative exon. *Mol Cell Biol* 15, 4825-34.

Del Gatto-Konczak, F., Olive, M., Gesnel, M. C., and Breathnach, R. (1999). hnRNP A1 recruited to an exon in vivo can function as an exon splicing silencer. *Mol Cell Biol* 19, 251-60.

Dempsey, L. A., Sun, H., Hanakahi, L. A., and Maizels, N. (1999). G4 DNA binding by LR1 and its subunits, nucleolin and hnRNP D, A role for G-G pairing in immunoglobulin switch recombination. *J Biol Chem* 274, 1066-71.

Dessau, W., Von Der Mark, H., Von Der Mark, K., and Fischer, S. (1980). Changes in the patterns of collagens and fibronectin during limb-bud chondrogenesis. *J. Embryol. Exp. Morphol.* 57, 51-60.

Dolnick, B. J. (1993). Cloning and characterization of natural occurring natural antisense RNA to human thymidylate synthase RNA. *Nucleic Acids Research* 21, 1747-1752.

Dono, R., and Zeller, R. (1994). Cell-type-specific nuclear translocation of fibroblast growth factor-2 isoforms during chicken kidney and limb morphogenesis. *Dev Biol* 163, 316-30.

Downie, S. A. (1994) Cellular and molecular differences between fore and hind limb precartilage mesenchyme: relation to skeletal pattern formation. In "Cell Biology and Anatomy", pp. 51. New York Medical College, Valhalla, N.Y.

Downie, S. A., and Newman, S. A. (1994). Morphogenetic differences between fore and hind limb precartilage mesenchyme: relation to mechanisms of skeletal pattern formation. *Dev. Biol.* 162, 195-208.

Downie, S. A., and Newman, S. A. (1995). Different roles for fibronectin in the generation of fore and hind limb precartilage condensations. *Developmental Biology* 172, 519-530.

Doye, V., and Hurt, E. (1997). From nucleoporins to nuclear pore complexes. *Curr Opin Cell Biol* 9, 401-11.

Dreyfuss, G. (1986). Structure and function of nuclear and cytoplasmic ribonucleoprotein particles. *Annu Rev Cell Biol* 2, 459-98.

Dreyfuss, G., Matunis, M. J., Pinol-Roma, S., and Burd, C. G. (1993). hnRNP proteins and the biogenesis of mRNA. *Annu. Rev. Biochem.* 62, 289-321.

Dreyfuss, G., Swanson, M. S., and Pinol-Roma, S. (1988). Heterogeneous nuclear ribonucleoprotein particles and the pathway of mRNA formation. *Trends Biochem Sci* 13, 86-91.

Eckenstein, F. P. (1994). Fibroblast growth factors in the nervous system. *J Neurobiol* 25, 1467-80.

Eckner, R., Ellmeier, W., and Birnstiel, M. L. (1991). Mature mRNA 3' end formation stimulates RNA export from the nucleus. *Embo J* 10, 3513-22.

Elicone, C., Lui, M., Geromanos, S., Erdjument-Bromage, H., and Tempst, P. (1994). Microbore reversed-phase high-performance liquid chromatographic purification of peptides for combined chemical sequencing-laser-desorption mass spectrometric analysis. *J Chromatogr A* 676, 121-37.

Ellerbrok, H., Serpente, N., Pancino, G., Vanhee, C., D'Auriol, L., Sitbon, M., and Vaquero, C. (1993). Sequences in the rev-responsive element responsible for premature translational arrest in the human-immunodeficiency-virus-type-1 envelope. *Eur J Biochem* 216, 459-67.

Eperon, I. C., Ireland, D. C., Smith, R. A., Mayeda, A., and Krainer, A. R. (1993). Pathways for selection of 5' splice sites by U1 snRNPs and SF2/ASF. *Embo J* 12, 3607-17.

Fallon, J. F., Lopez, A., Ros, M. A., Savage, M. P., Olwin, B. B., and Simandl, B. K. (1994). FGF-2: apical ectodermal ridge growth signal for chick limb development. *Science.* 264, 104-107.

Faura, M., Renau-Piqueras, J., Bachs, O., and Bosser, R. (1995). Differential distribution of heterogeneous nuclear ribonucleoproteins in rat tissues. *Biochem Biophys Res Commun* 217, 554-60.

Fischer, U., Huber, J., Boelens, W. C., Maftaj, I. W., and Luhrmann, R. (1995). The HIV-1 Rev activation domain is a nuclear export signal that accesses an export pathway used by specific cellular RNAs. *Cell* 82, 475-83.

Fogerty, F. J., and Mosher, D. F. (1990). Mechanisms for organization of fibronectin matrix. *Cell Differ Dev* 32, 439-50.

Fornerod, M., Ohno, M., Yoshida, M., and Mattaj, I. W. (1997). CRM1 is an export receptor for leucine-rich nuclear export signals [see comments]. *Cell* 90, 1051-60.

Frenz, D. A., Akiyama, S. K., Paulsen, D. F., and Newman, S. A. (1989a). Latex beads as probes of cell surface-extracellular matrix interactions during chondrogenesis: evidence for a role for amino-terminal heparin-binding domain of fibronectin. *Dev. Biol.* 136, 87-96.

Frenz, D. A., Jaikaria, N. S., and Newman, S. A. (1989b). The mechanism of precartilage mesenchymal condensation: a major role for interaction of the cell surface with the amino-terminal heparin-binding domain of fibronectin. *Dev. Biol.* 136, 97-103.

Fridell, R. A., Truant, R., Thorne, L., Benson, R. E., and Cullen, B. R. (1997). Nuclear import of hnRNP A1 is mediated by a novel cellular cofactor related to karyopherin-beta. *J Cell Sci* 110, 1325-31.

Fu, X. D. (1995). The superfamily of arginine/serine-rich splicing factors. *RNA* 1, 663-680.

Fukuda, M., Asano, S., Nakamura, T., Adachi, M., Yoshida, M., Yanagida, M., and Nishida, E. (1997). CRM1 is responsible for intracellular transport mediated by the nuclear export signal. *Nature* 390, 308-11.

Gallego, M. E., Sirand-Pugnet, P., Durosay, P., Clouet d'Orval, B., d'Aubenton-Carafa, Y., Brody, E., Expert-Bezancon, A., and Marie, J. (1996). Tissue-specific splicing of two mutually exclusive exons of the chicken beta-tropomyosin pre-mRNA: positive and negative regulations. *Biochimie* 78, 457-65.

Gardner, R. L. (1983). *International Review of Experimental Pathology* 24, 63-133.

Ge, H., and Manley, J. L. (1990). A protein factor, ASF, controls cell-specific alternative splicing of SV40 early pre-mRNA in vitro. *Cell* 62, 25-34.

Gilbert, S. F. (1997). "Developmental biology." Sinauer Associates, Sunderland, Mass.

Glant, T. T., Hadhazy, C. S., Mikecz, K., and Sipos, A. (1985). Appearance and persistence of fibronectin in cartilage. Specific interaction of fibronectin with collage type II. *Histochemistry* 82, 149-158.

Goldfarb, D. S. (1997). Nuclear transport: proliferating pathways. *Curr Biol* 7, R13-6.

Gorlich, D. (1997). Nuclear protein import. *Curr Opin Cell Biol* 9, 412-9.

Gorlich, D., and Mattaj, I. W. (1996). Nucleocytoplasmic transport. *Science* 271, 1513-8.

Gould, S. E., Upholt, W. B., and Kosher, R. A. (1995). Characterization of chicken syndecan-3 as a heparan sulfate proteoglycan and its expression during embryogenesis. *Dev. Biol.* 168, 438-451.

Graham, I. R., Hamshere, M., and Eperon, I. C. (1992). Alternative splicing of a human alpha-tropomyosin muscle-specific exon: identification of determining sequences. *Mol Cell Biol* 12, 3872-82.

Greeve, J., Lellek, H., Rautenberg, P., and Greten, H. (1998). Inhibition of the apolipoprotein B mRNA editing enzyme-complex by hnRNP C1 protein and 40S hnRNP complexes. *Biol Chem* 379, 1063-73.

Grothe, C., and Meisinger, C. (1995). Fibroblast growth factor (FGF)-2 sense and antisense mRNA and FGF receptor type 1 mRNA are present in the embryonic and adult rat nervous system: specific detection by nuclease protection assay. *Neurosci Lett* 197, 175-8.

Haines, D. S., Strauss, K. I., and Gillespie, D. H. (1991). Cellular response to double-stranded RNA. *J Cell Biochem* 46, 9-20.

Hajihosseini, M. K., and Dickson, C. (1999). A subset of fibroblast growth factors (Fgfs) promote survival, but Fgf-8b specifically promotes astroglial differentiation of rat cortical precursor cells. *Mol Cell Neurosci* 14, 468-85.

Hall, B. K. (1983). Cartilage: Development, Differentiation, and Growth, Vol. Two. Academic Press, New York.

Hall, B. K., and Miyake, T. (1992). The membranous skeleton: the role of cell condensations in vertebrate skeletogenesis. *Anat Embryol. Berl.* 186, 107-124.

Hamburger, V., and Hamilton, H. L. (1951). A series of normal stages in the development of the chick embryo. *J. Morphol.* 88, 49-92.

Hamm, J., and Mattaj, I. W. (1990). Monomethylated cap structures facilitate RNA export from the nucleus. *Cell* 63, 109-18.

Han, J. K. (1997). Expression of the fibroblast growth factor-2 gene during chick development. *Mol Cells* 7, 208-13.

Hassfeld, W., Chan, E. K. L., Mathison, D. A., Portman, D., Dreyfuss, G., Steiner, G., and Tan, E. M. (1998). Molecular definition of heterogeneous nuclear ribonucleoprotein R (hnRNP R) using autoimmune antibody: immunological relationship with hnRNP P. *Nucleic Acids Res* 26, 439-45.

Herold, A., Truant, R., Wiegand, H., and Cullen, B. R. (1998). Determination of the functional domain organization of the importin alpha nuclear import factor. *J Cell Biol* 143, 309-18.

Higuchi, M., Single, F. N., Kohler, M., Sommer, B., Sprengel, R., and Seeburg, P. H.

(1993). RNA editing of AMPA receptor subunit GluR-B: a base-paired intron-exon structure determines position and efficiency. *Cell* 75, 1361-70.

Hildebrandt, M., and Nellen, W. (1992). Differential antisense transcription from the Dictyostelium EB4 gene locus: implications on antisense-mediated regulation of mRNA stability. *Cell* 69, 197-204.

Honore, B., Vorum, H., and Baandrup, U. (1999). hnRNPs H, H' and F behave differently with respect to posttranslational cleavage and subcellular localization. *FEBS Lett* 456, 274-80.

Hopper, A. K., Traglia, H. M., and Dunst, R. W. (1990). The yeast RNA1 gene product necessary for RNA processing is located in the cytosol and apparently excluded from the nucleus. *J Cell Biol* 111, 309-21.

Hu, M. C., Qiu, W. R., Wang, Y. P., Hill, D., Ring, B. D., Scully, S., Bolon, B., DeRose, M., Luethy, R., Simonet, W. S., Arakawa, T., and Danilenko, D. M. (1998). FGF-18, a novel member of the fibroblast growth factor family, stimulates hepatic and intestinal proliferation. *Mol Cell Biol* 18, 6063-74.

Huang, Y., and Carmichael, G. C. (1996). Role of polyadenylation in nucleocytoplasmic transport of mRNA. *Mol Cell Biol* 16, 1534-42.

Hynes, R. O. (1990). "Fibronectins." Springer-Verlag, New York.

Idriss, H., Kumar, A., Casas-Finet, J. R., Guo, H., Damuni, Z., and Wilson, S. H. (1994). Regulation of in vitro nucleic acid strand annealing activity of heterogeneous nuclear ribonucleoprotein protein A1 by reversible phosphorylation. *Biochemistry* 33, 11382-90.

Ignotz, R. A., Endo, T., and Massague, J. (1987). Regulation of fibronectin and type I collagen mRNA levels by transforming growth factor-beta. *J. Biol. Chem.* 262, 6643-6646.

Inoue, K., Hoshijima, K., Sakamoto, H., and Shimura, Y. (1990). Binding of the Drosophila sex-lethal gene product to the alternative splice site of transformer primary transcript. *Nature* 344, 461-3.

Izaurralde, E., Jarmolowski, A., Beisel, C., Mattaj, I. W., Dreyfuss, G., and Fischer, U. (1997a). A role for the M9 transport signal of hnRNP A1 in mRNA nuclear export. *J Cell Biol* 137, 27-35.

Izaurralde, E., Kutay, U., von Kobbe, C., Mattaj, I. W., and Gorlich, D. (1997b). The asymmetric distribution of the constituents of the Ran system is essential for transport into and out of the nucleus. *Embo J* 16, 6535-47.

Izaurralde, E., McGuigan, C., and Mattaj, I. W. (1995). Nuclear localization of a cap-binding protein complex. *Cold Spring Harb Symp Quant Biol* 60, 669-75.

Jang, J. H., Wang, F., and Kan, M. (1997). Heparan sulfate is required for interaction and activation of the epithelial cell fibroblast growth factor receptor-2111b with stromal-derived fibroblast growth factor-7. *In Vitro Cell Dev Biol Anim* 33, 819-24.

Jarmolowski, A., Boelens, W. C., Izaurralde, E., and Mattaj, I. W. (1994). Nuclear export of different classes of RNA is mediated by specific factors. *J Cell Biol* 124, 627-35.

Johnson, D. E., and Williams, L. T. (1993). Structural and functional diversity in the FGF receptor multigene family. *Adv Cancer Res* 60, 1-41.

Joseph-Silverstein, J., Consigli, S. A., Lyser, K. M., and Ver Pault, C. (1989). *Journal of Cell Biology*, 2459-2466.

Jung, J., Zheng, M., Goldfarb, M., and Zaret, K. S. (1999). Initiation of mammalian liver development from endoderm by fibroblast growth factors. *Science* 284, 1998-2003.

Kaffman, A., Rank, N. M., O'Neill, E. M., Huang, L. S., and O'Shea, E. K. (1998). The receptor Msn5 exports the phosphorylated transcription factor Pho4 out of the nucleus. *Nature* 396, 482-6.

Kalderon, D., Roberts, B. L., Richardson, W. D., and Smith, A. E. (1984). A short amino acid sequence able to specify nuclear location. *Cell* 39, 499-509.

Kamma, H., Horiguchi, H., Wan, L., Matsui, M., Fujiwara, M., Fujimoto, M., Yazawa, T., and Dreyfuss, G. (1999). Molecular characterization of the hnRNP A2/B1 proteins: tissue-specific expression and novel isoforms. *Exp Cell Res* 246, 399-411.

Kamma, H., Portman, D. S., and Dreyfuss, G. (1995). Cell type-specific expression of hnRNP proteins. *Exp Cell Res* 221, 187-96.

Kardon, G. (1998). Muscle and tendon morphogenesis in the avian hind limb. *Development* 125, 4019-32.

Kasashima, K., Terashima, K., Yamamoto, K., Sakashita, E., and Sakamoto, H. (1999). Cytoplasmic localization is required for the mammalian ELAV-like protein HuD to induce neuronal differentiation. *Genes Cells* 4, 667-683.

Kaufman, M. H. a. B., J. B. L. (1999). "The Anatomical Basis of Mouse DevelopmentThe Anatomical Basis of Mouse Development." Academic Press, New Yok.

Kay, B. K., Sawhney, R. K., and Wilson, S. H. (1990). Potential for two isoforms of the A1 ribonucleoprotein in *Xenopus laevis*. *Proc Natl Acad Sci U S A* 87, 1367-71.

Kettunen, P., Karavanova, I., and Thesleff, I. (1998). Responsiveness of developing dental tissues to fibroblast growth factors: expression of splicing alternatives of FGFR1, -2, -3, and of FGFR4; and stimulation of cell proliferation by FGF-2, -4, -8, and -9. *Dev Genet* 22, 374-85.

Kiledjian, M., Burd, C. G., Portman, D. S., and Dreyfuss, G. (1994). Structure and Function of hnRNP Proteins. In "Frontiers in Molecular Biology" (K. a. M. Nagai, I. W., Ed.), pp. 127-149. Oxford: IRL Press.

Kiledjian, M., and Dreyfuss, G. (1992). Primary structure and binding activity of the hnRNP U protein: binding RNA through RGG box. *Embo J* 11, 2655-64.

Kimelman, D., and Kirschner, M. (1987). Synergistic induction of mesoderm by FGF and TGF-beta and the identification of an mRNA coding for FGF in the early Xenopus embryo. *Cell* 51, 869-77.

Kimelman, D., and Kirschner, M. W. (1989). An antisense mRNA directs the covalent modification of the transcript encoding fibroblast growth factor in Xenopus oocytes. *Cell* 59, 687-96.

Kishore, R., Bronstein, N., Ismail, Z., Zhang, Q., Taylor, T., and Newman, S. A. (Submitted for publication). Spatiotemporal regulation and in vitro expression of avian hnRNP A1, an mRNA shuttle protein-exon splicing silencer.

Kishore, R., Samuel, M., Khan, M. Y., Hand, J., Frenz, D. A., and Newman, S. A. (1997). Interaction of the NH2-terminal domain of fibronectin with heparin: role of the O-loops of the type I modules. *J. Biol. Chem.* 272, 17078-17085.

Knee, R., and Murphy, P. R. (1997). Regulation of gene expression by natural antisense RNA transcripts. *Neurochem Int* 31, 379-92.

Kosher, R. A., Walker, K. H., and Ledger, P. W. (1982). Temporal and spatial distribution of fibronectin during development of the embryonic chick limb bud. *Cell. Differ.* 11, 217-228.

Krainer, A. R., Conway, G. C., and Kozak, D. (1990). The essential pre-mRNA splicing factor SF2 influences 5' splice site selection by activating proximal sites. *Cell* 62, 35-42.

Kulyk, W. M., Rodgers, B. J., Greer, K., and Kosher, R. A. (1989). Promotion of embryonic chick limb cartilage differentiation by transforming growth factor-beta. *Dev. Biol.* 135, 424-430.

Kumar, A., Williams, K. R., and Szer, W. (1986). Purification and domain structure of core hnRNP proteins A1 and A2 and their relationship to single-stranded DNA-binding proteins. *J Biol Chem* 261, 11266-73.

Kumar, A., and Wilson, S. H. (1990). Studies of the strand-annealing activity of mammalian hnRNP complex protein A1. *Biochemistry*. 29, 10717-10722.

Kutay, U., Bischoff, F. R., Kostka, S., Kraft, R., and Gorlich, D. (1997). Export of importin alpha from the nucleus is mediated by a specific nuclear transport factor [see comments]. *Cell* 90, 1061-71.

Kutay, U., Lipowsky, G., Izaurralde, E., Bischoff, F. R., Schwarzmaier, P., Hartmann, E., and Gorlich, D. (1998). Identification of a tRNA-specific nuclear export receptor. *Mol Cell* 1, 359-69.

Larsen, W. J. (1997). "Human Embryology." Churchill Livingston, N.Y.

Lazar, M. A., Hodin, R. A., Cardona, G., and Chin, W. W. (1990). Gene expression from the c-erbA alpha/Rev-ErbA alpha genomic locus. Potential regulation of alternative splicing by opposite strand transcription. *J Biol Chem* 265, 12859-63.

Leonard, C. M., Fuld, H. M., Frenz, D. A., Downie, S. A., Massague, J., and Newman, S. A. (1991). Role of transforming growth factor-beta in chondrogenic pattern formation in the embryonic limb: stimulation of mesenchymal condensation and fibronectin gene expression by exogenous TGF-beta and evidence for endogenous TGF-beta-like activity. *Dev. Biol.* 145, 99-109.

Leonard, C. M., and Newman, S. A. (1987). Nuclear events during early chondrogenesis: phosphorylation of the pre-cartilage 35.5-kDa domain-specific chromatin protein and its regulation by cyclic AMP. *Dev. Biol.* 120, 92-100.

Lin, X., Buff, E. M., Perrimon, N., and Michelson, A. M. (1999). Heparan sulfate proteoglycans are essential for FGF receptor signaling during Drosophila embryonic development. *Development* 126, 3715-23.

Linkhart, T. A., Clegg, C. H., and Hauschika, S. D. (1981). Myogenic differentiation in permanent clonal mouse myoblast cell lines: regulation by macromolecular growth factors in the culture medium. *Dev Biol* 86, 19-30.

Lizarraga, G., Ferrari, D., Kalinowski, M., Ohuchi, H., Noji, S., Kosher, R. A., and Dealy, C. N. (1999). FGFR2 signaling in normal and limbless chick limb buds. *Dev Genet* 25, 331-8.

Lopez, A. J. (1998). Alternative splicing of pre-mRNA: developmental consequences and mechanisms of regulation. *Annu Rev Genet* 32, 279-305.

Luhrmann, R. (1990). Functions of U-snRNPs. *Mol Biol Rep* 14, 183-92.

Lynch, K. W., and Maniatis, T. (1995). Synergistic interactions between two distinct elements of a regulated splicing enhancer. *Genes Dev* 9, 284-93.

Lynch, K. W., and Maniatis, T. (1996). Assembly of specific SR protein complexes on distinct regulatory elements of the Drosophila doublesex splicing enhancer. *Genes Dev* 10, 2089-101.

MacCabe, J. A., Blaylock, R. L., Jr., Latimer, J. L., and Pharris, L. J. (1991). Fibroblast growth factor and culture in monolayer rescue mesoderm cells destined to die in the developing avian wing. *J Exp Zool* 257, 208-13.

Mackem, S., and Mahon, K. A. (1991). Ghox 4.7: A chick homeobox gene expressed primarily in limb buds with limb-type differences in expression. *Development* 112, 791-806.

Mahajan, R., Delphin, C., Guan, T., Gerace, L., and Melchior, F. (1997). A small ubiquitin-related polypeptide involved in targeting RanGAP1 to nuclear pore complex protein RanBP2. *Cell* 88, 97-107.

Makarenkova, H., and Patel, K. (1999). Gap junction signalling mediated through connexin-43 is required for chick limb development. *Dev Biol* 207, 380-92.

Manche, L., Green, S. R., Schmedt, C., and Mathews, M. B. (1992). Interactions between double-stranded RNA regulators and the protein kinase DAI. *Mol Cell Biol* 12, 5238-48.

Manley, J. L., and Tacke, R. (1996). SR proteins and splicing control. *Genes Dev* 10, 1569-79.

Martinez, S., Crossley, P. H., Cobos, I., Rubenstein, J. L., and Martin, G. R. (1999). FGF8 induces formation of an ectopic isthmic organizer and isthmocerebellar development via a repressive effect on Otx2 expression. *Development* 126, 1189-200.

Massague, J. (1987). The TGF-beta family of growth and differentiation factors. *Cell.* 49, 437-438.

Matunis, E. L., Matunis, M. J., and Dreyfuss, G. (1992). Characterization of the major hnRNP proteins from *Drosophila melanogaster*. *J Cell Biol* 116, 257-69.

Matunis, M. J., Coutavas, E., and Blobel, G. (1996). A novel ubiquitin-like modification modulates the partitioning of the Ran-GTPase-activating protein RanGAP1 between the cytosol and the nuclear pore complex. *J Cell Biol* 135, 1457-70.

Mayeda, A., Helfman, D. M., and Krainer, A. R. (1993). Modulation of exon skipping and inclusion by heterogeneous nuclear ribonucleoprotein A1 and pre-mRNA splicing factor SF2/ASF [published erratum appears in Mol Cell Biol 1993 Jul;13(7):4458]. *Mol Cell Biol* 13, 2993-3001.

Mayeda, A., and Krainer, A. R. (1992). Regulation of alternative pre-mRNA splicing by hnRNP A1 and splicing factor SF2. *Cell* 68, 365-75.

Mayeda, A., Munroe, S. H., Caceres, J. F., and Krainer, A. R. (1994). Function of conserved domains of hnRNP A1 and other hnRNP A/B proteins. *Embo J* 13, 5483-95.

Melcher, T., Maas, S., Higuchi, M., Keller, W., and Seeburg, P. H. (1995). Editing of alpha-amino-3-hydroxy-5-methylisoxazole-4-propionic acid receptor GluR-B pre-mRNA in vitro reveals site-selective adenosine to inosine conversion. *J Biol Chem* 270, 8566-70.

Melchior, F., and Gerace, L. (1998). Two-way trafficking with Ran. *Trends Cell Biol* 8, 175-9.

Melchior, F., Paschal, B., Evans, J., and Gerace, L. (1993). Inhibition of nuclear protein import by nonhydrolyzable analogues of GTP and identification of the small GTPase Ran/TC4 as an essential transport factor [published erratum appears in J Cell Biol 1994 Jan; 124(1-2):217]. *J Cell Biol* 123, 1649-59.

Merino, E., Balbas, P., Puente, J. L., and Bolivar, F. (1994). Antisense overlapping open reading frames in genes from bacteria to humans. *Nucleic Acids Res* 22, 1903-8.

Merrill, B. M., Stone, K. L., Cobianchi, F., Wilson, S. H., and Williams, K. R. (1988). Phenylalanines that are conserved among several RNA-binding proteins form part of a nucleic acid-binding pocket in the A1 heterogeneous nuclear ribonucleoprotein. *J Biol Chem* 263, 3307-13.

Michael, W. M., Choi, M., and Dreyfuss, G. (1995). A nuclear export signal in hnRNP A1: a signal-mediated, temperature-dependent nuclear protein export pathway. *Cell* 83, 415-22.

Michael, W. M., Eder, P. S., and Dreyfuss, G. (1997). The K nuclear shuttling domain: a novel signal for nuclear import and nuclear export in the hnRNP K protein. *Embo J* 16, 3587-98.

Miki, T., Bottaro, D. P., Fleming, T. P., Smith, C. L., Burgess, W. H., Chan, A. M., and Aaronson, S. A. (1992). Determination of ligand-binding specificity by alternative splicing: two distinct growth factor receptors encoded by a single gene. *Proc Natl Acad Sci U S A* 89, 246-50.

Min, H., Turck, C. W., Nikolic, J. M., and Black, D. L. (1997). A new regulatory protein, KSRP, mediates exon inclusion through an intronic splicing enhancer. *Genes and Development* 11, 1023-1036.

Miralles, F., Czernichow, P., and Scharfmann, R. (1999). Pancreatic acinar AR42J cells express functional nerve growth factor receptors. *J Endocrinol* 160, 433-42.

Miura, T., and Shiota, K. (2000). Extracellular matrix environment influences chondrogenic pattern formation in limb bud micromass culture: Experimental verification of theoretical models. *Anat Rec* 258, 100-107.

Miyajima, N., Horiuchi, R., Shibuya, Y., Fukushige, S., Matsubara, K., Toyoshima, K., and Yamamoto, T. (1989). Two erbA homologs encoding proteins with different T3 binding capacities are transcribed from opposite DNA strands of the same genetic locus. *Cell* 57, 31-9.

Montecucco, C., Caporali, R., Cobianchi, F., and Biamonti, G. (1996). Identification of autoantibodies to the I protein of the heterogeneous nuclear ribonucleoprotein complex in patients with systemic sclerosis. *Arthritis Rheum* 39, 1669-76.

Moore, M. S., and Blobel, G. (1993). The GTP-binding protein Ran/TC4 is required for protein import into the nucleus. *Nature* 365, 661-3.

Mosher, D. F. (1984). Physiology of fibronectin. *Annu Rev Med* 35, 561-75.

Munroe, S. H., and Dong, X. F. (1992). Heterogeneous nuclear ribonucleoprotein A1 catalyzes RNA.RNA annealing. *Proc Natl Acad Sci U S A* 89, 895-9.

Murphy, P. R., and Knee, R. S. (1994). Identification and characterization of an antisense RNA transcript (gfg) from the human basic fibroblast growth factor gene. *Mol Endocrinol* 8, 852-9.

Nakielny, S., and Dreyfuss, G. (1997a). Import and export of the nuclear protein import receptor transportin by a mechanism independent of GTP hydrolysis. *Curr Biol* 8, 89-95.

Nakielny, S., and Dreyfuss, G. (1997b). Nuclear export of proteins and RNAs. *Curr Opin Cell Biol* 9, 420-9.

Nakielny, S., Shaikh, S., Burke, B., and Dreyfuss, G. (1999). Nup153 is an M9-containing mobile nucleoporin with a novel Ran-binding domain. *Embo J* 18, 1982-95.

Nakielny, S., Siomi, M. C., Siomi, H., Michael, W. M., Pollard, V., and Dreyfuss, G. (1996). Transportin: nuclear transport receptor of a novel nuclear protein import pathway. *Exp Cell Res* 229, 261-6.

Nellen, W., and Lichtenstein, C. (1993). What makes an mRNA anti-sense-itive? *Trends Biochem Sci* 18, 419-23.

Neville, M., Stutz, F., Lee, L., Davis, L. I., and Rosbash, M. (1997). The importin-beta family member Crm1p bridges the interaction between Rev and the nuclear pore complex during nuclear export. *Curr Biol* 7, 767-75.

Newman, S. A. (1977). Lineage and pattern in the developing wing bud. In "Vertebrate Limb and Somite Morphogenesis" (D. A. Ede, J. R. Hinchliffe, and M. Balls, Eds.), pp. 181-197. Cambridge University Press, Cambridge.

Newman, S. A. (1988). Lineage and pattern in the developing vertebrate limb. *Trends. Genet.* 4, 329-332.

Newman, S. A. (1996). Sticky fingers: Hox genes and cell adhesion in vertebrate limb development. *BioEssays* 18, 171-174.

Newman, S. A., Frisch, H. L., Perle, M. A., and Tomasek, J. J. (1981a). Limb development: Aspects of differentiation, pattern formation and morphogenesis. In "Morphogenesis and Pattern Formation" (T. G. Connolly, L. L. Brinkley, and B. M. Carlson, Eds.), pp. 163-178. Raven Press, New York.

Newman, S. A., Pautou, M. -P., and Kieny, M. (1981b). The distal boundary of myogenic primordia in chimeric avian limb buds and its relation to an accessible population of cartilage progenitor cells. *Dev. Biol.* 84, 440-448.

Newman, S. A., and Tomasek, J. J. (1996). Morphogenesis of connective tissues. In "Extracellular Matrices" (W. D. Comper, Ed.), Vol. 2: Molecular Components and Interactions, pp. 335-369. Harwood Academic Publishers, Reading, U.K.

Nigg, E. A. (1997). Nucleocytoplasmic transport: signals, mechanisms and regulation. *Nature* 386, 779-87.

Niswander, L., and Martin, G. R. (1992). Fgf-4 expression during gastrulation, myogenesis, limb and tooth development in the mouse. *Development* 114, 755-68.

Niswander, L., Tickle, C., Vogel, A., Booth, I., and Martin, G. R. (1993). FGF-4 replaces the apical ectodermal ridge and directs outgrowth and patterning of the limb. *Cell.* 75, 579-587.

Noji, S., Koyama, E., Myokai, F., Nohno, T., Ohuchi, H., Nishikawa, K., and Taniguchi, S. (1993). Differential expression of three chick FGF receptor genes, FGFR1, FGFR2 and FGFR3, in limb and feather development. *Prog Clin Biol Res*, 645-54.

Oberlender, S. A., and Tuan, R. S. (1994). Expression and functional involvement of N-cadherin in embryonic limb chondrogenesis. *Development* 120, 177-187.

Oberosler, P., and Nellen, W. (1997). Functional activity and developmental regulation of DdRBP1, a RNA binding protein in *Dictyostelium discoideum*. *Biol Chem* 378, 1353-60.

Ohbayashi, N., Hoshikawa, M., Kimura, S., Yamasaki, M., Fukui, S., and Itoh, N. (1998). Structure and expression of the mRNA encoding a novel fibroblast growth factor, FGF18. *J Biol Chem* 273, 18161-4.

Ohtsubo, M., Kai, R., Furuno, N., Sekiguchi, T., Sekiguchi, M., Hayashida, H., Kuma, K., Miyata, T., Fukushige, S., Murotsu, T., and et al. (1987). Isolation and characterization of the active cDNA of the human cell cycle gene (RCC1) involved in the regulation of onset of chromosome condensation. *Genes Dev* 1, 585-93.

Oldberg, A., and Ruoslahti, E. (1982). Interactions between chondroitin sulfate proteoglycan, fibronectin, and collagen. *J Biol Chem* 257, 4859-63.

Oldridge, M., Lunt, P. W., Zackai, E. H., McDonald-McGinn, D. M., Muenke, M., Moloney, D. M., Twigg, S. R., Heath, J. K., Howard, T. D., Hoganson, G., Gagnon, D. M., Jabs, E. W., and Wilkie, A. O. (1997). Genotype-phenotype correlation for nucleotide substitutions in the IgII-IgIII linker of FGFR2. *Hum Mol Genet* 6, 137-43.

Oldridge, M., Wilkie, A. O., Slaney, S. F., Poole, M. D., Pulleyn, L. J., Rutland, P., Hockley, A. D., Wake, M. J., Goldin, J. H., Winter, R. M., and et al. (1995). Mutations in the third immunoglobulin domain of the fibroblast growth factor receptor-2 gene in Crouzon syndrome. *Hum Mol Genet* 4, 1077-82.

Oldridge, M., Zackai, E. H., McDonald-McGinn, D. M., Iseki, S., Morriss-Kay, G. M., Twigg, S. R., Johnson, D., Wall, S. A., Jiang, W., Theda, C., Jabs, E. W., and Wilkie, A. O. (1999). De novo alu-element insertions in FGFR2 identify a distinct pathological basis for Apert syndrome. *Am J Hum Genet* 64, 446-61.

Olwin, B. B., Arthur, K., Hannon, K., Hein, P., McFall, A., Riley, B., Szebenyi, G., Zhou, Z., Zuber, M. E., Rapraeger, A. C., and et al. (1994). Role of FGFs in skeletal muscle and limb development. *Mol Reprod Dev* 39, 90-100; discussion 100-1.

Ornitz, D. M. (2000). FGFs, heparan sulfate and FGFRs: complex interactions essential for development. *Bioessays* 22, 108-112.

Orr-Urtreger, A., Bedford, M. T., Burakova, T., Arman, E., Zimmer, Y., Yayon, A., Givol, D., and Lonai, P. (1993). Developmental localization of the splicing alternatives of fibroblast growth factor receptor-2 (FGFR2). *Dev Biol* 158, 475-86.

Orr-Urtreger, A., Givol, D., Yayon, A., Yarden, Y., and Lonai, P. (1991). Developmental expression of two murine fibroblast growth factor receptors, flg and bek. *Development* 113, 1419-34.

Ossareh-Nasari, B., Bachelerie, F., and Dargemont, C. (1997). Evidence for a role of CRM1 in signal-mediated nuclear protein export. *Science* 278, 141-144.

Park, W. J., Theda, C., Maestri, N. E., Meyers, G. A., Fryburg, J. S., Dufresne, C., Cohen, M. M., Jr., and Jabs, E. W. (1995). Analysis of phenotypic features and FGFR2 mutations in Apert syndrome. *Am J Hum Genet* 57, 321-8.

Patstone, G., Pasquale, E. B., and Maher, P. A. (1993). Different members of the fibroblast growth factor receptor family are specific to distinct cell types in the developing chicken embryo. *Dev. Biol.* 155, 107-123.

Paulsen, D. F., and Solursh, M. (1988). Microtiter micromass cultures of limb-bud mesenchymal cells. In. Vitro. *Cell. Dev. Biol.* 24, 138-147.

Perle, M. A., Leonard, C. M., and Newman, S. A. (1982). Developmentally regulated nonhistone proteins: evidence for deoxyribonucleic acid binding role and localization near deoxyribonuclease I sensitive domains of precartilage cell chromatin. *Biochemistry*. 21, 2379-2386.

Perle, M. A., and Newman, S. A. (1980). Talpid$^2$ mutant of the chicken with perturbed cartilage development has an altered precartilage-specific chromatin protein. *Proc. Natl. Acad. Sci. U. S. A*, 77, 4828-4830.

Peters, K. G., Werner, S., Chen, G., and Williams, L. T. (1992). Two FGF receptor genes are differentially expressed in epithelial and mesenchymal tissues during limb formation and organogenesis in the mouse. *Development* 114, 233-43.

Pinol-Roma, S., Choi, Y. D., Matunis, M. J., and Dreyfuss, G. (1988). Immunopurification of heterogeneous nuclear ribonucleoprotein particles reveals an assortment of RNA-binding proteins [published erratum appears in Genes Dev 1988 Apr;2(4):490]. *Genes Dev* 2, 215-27.

Pinol-Roma, S., and Dreyfuss, G. (1991). Transcription-dependent and transcription-independent nuclear transport of hnRNP proteins. *Science* 253, 312-4.

Pinol-Roma, S., and Dreyfuss, G. (1992). Shuttling of pre-mRNA binding proteins between nucleus and cytoplasm. *Nature* 355, 730-2.

Pinol-Roma, S., Swanson, M. S., Gall, J. G., and Dreyfuss, G. (1989). A novel heterogeneous nuclear RNP protein with a unique distribution on nascent transcripts. *J Cell Biol* 109, 2575-87.

Pollard, V. W., Michael, W. M., Nakielny, S., Siomi, M. C., Wang, F., and Dreyfuss, G. (1996). A novel receptor-mediated nuclear protein import pathway. *Cell* 86, 985-94.

Pontius, B. W., and Berg, P. (1990). Renaturation of complementary DNA strands mediated by purified mammalian heterogeneous nuclear ribonucleoprotein A1 protein: implications for a mechanism for rapid molecular assembly. *Proc Natl Acad Sci U S A* 87, 8403-7.

Portman, D. S., and Dreyfuss, G. (1994). RNA annealing activities in HeLa nuclei. *Embo J* 13, 213-21.

Rabbitts, T. H., Forster, A., Larson, R., and Nathan, P. (1993). Fusion of the dominant negative transcription regulator CHOP with a novel gene FUS by translocation t(12;16) in malignant liposarcoma. *Nat Genet* 4, 175-80.

Radu, A., Moore, M. S., and Blobel, G. (1995). The peptide repeat domain of nucleoporin Nup98 functions as a docking site in transport across the nuclear pore complex. *Cell* 81, 215-22.

Rappolee, D. A., Basilico, C., Patel, Y., and Werb, Z. (1994). Expression and function of FGF-4 in peri-implantation development in mouse embryos. *Development* 120, 2259-69.

Riley, B. B., Savage, M. P., Simandl, B. K., Olwin, B. B., and Fallon, J. F. (1993). Retroviral expression of FGF-2 (bFGF) affects patterning in chick limb bud. *Development* 118, 95-104.

Robbins, J., Dilworth, S. M., Laskey, R. A., and Dingwall, C. (1991). Two interdependent basic domains in nucleoplasmin nuclear targeting sequence: identification of a class of bipartite nuclear targeting sequence. *Cell* 64, 615-23.

Robinow, S., and White, K. (1988). The locus elav of *Drosophila melanogaster* is expressed in neurons at all developmental stages. *Dev Biol* 126, 294-303.

Roth, M. B., Zahler, A. M., and Stolk, J. A. (1991). A conserved family of nuclear phosphoproteins localized to sites of polymerase II transcription. *J Cell Biol* 115, 587-96.

Rout, M. P., Blobel, G., and Aitchison, J. D. (1997). A distinct nuclear import pathway used by ribosomal proteins. *Cell* 89, 715-25.

Rubin, J. S., Osada, H., Finch, P. W., Taylor, W. G., Rudikoff, S., and Aaronson, S. A. (1989). Purification and characterization of a newly identified growth factor specific for epithelial cells. *Proc Natl Acad Sci U S A* 86, 802-6.

Rush, M. G., Drivas, G., and D'Eustachio, P. (1996). The small nuclear GTPase Ran: how much does it run? *Bioessays* 18, 103-12.

Saccone, S., Biamonti, G., Maugeri, S., Bassi, M. T., Bunone, G., Riva, S., and Della Valle, G. (1992). Assignment of the human heterogeneous nuclear ribonucleoprotein A1 gene (HNRPA1) to chromosome 12q13.1 by cDNA competitive in situ hybridization. *Genomics* 12, 171-4.

Sadiq, M., Hildebrandt, M., Maniak, M., and Nellen, W. (1994). Developmental regulation of antisense-mediated gene silencing in Dictyostelium. *Antisense Res Dev* 4, 263-7.

Sambrook, J., Fritsch, E. F., and Maniatis, T. (1989). "Molecular Cloning. A Laboratory Manual." Cold Spring Harbor Laboratory Press, Cold Spring Harbor.

Sanger, F., Nicklen, S., and Coulson, A. R. (1977). DNA sequencing with chain-terminating inhibitors. *Proc. Natl. Acad. Sci. U. S. A.* 74, 5463-5467.

Saunders, J. W., Jr. (1948). The proximo-distal sequence of origin of the parts of the chick wing and the role of the ectoderm. *J. Exp. Zool.* 108, 363-402.

Savage, M. P., and Fallon, J. F. (1995). FGF-2 mRNA and its antisense message are expressed in a developmentally specific manner in the chick limb bud and mesonephros. *Dev. Dyn.* 202, 343-353.

Savage, M. P., Hart, C. E., Riley, B. B., Sasse, J., Olwin, B. B., and Fallon, J. F. (1993). Distribution of FGF-2 suggests it has a role in chick limb bud growth. *Dev. Dyn.* 198, 159-170.

Schofield, J. N., and Wolpert, L. (1990). Effect of TGF-beta 1, TGF-beta 2, and bFGF on chick cartilage and muscle cell differentiation. *Exp Cell Res* 191, 144-8.

Scotet, E., Reichmann, R., Breathnach, R., and Houssaint, E. (1995). Oncoprotein fos activation in epithelial cells induces and epithelio-mensenchymal conversion and changes the receptor encoded by the FGFR-2 mRNA from K-SAM to BEK. *Oncology Report* 2, 203-207.

Serrero, G., and Khoo, J. C. (1982). An in vitro model to study adipose differentiation in serum-free medium. *Anal Biochem* 120, 351-9.

Seyedin, S. M., Segarini, P. R., Rosen, D. M., Thompson, A. Y., Bentz, H., and Graycar, J. (1987). Cartilage-inducing factor-B is a unique protein structurally and functionally related to transforming growth factor-beta. *J Biol Chem* 262, 1946-9.

Shamim, H., Mahmood, R., Logan, C., Doherty, P., Lumsden, A., and Mason, I. (1999). Sequential roles for Fgf4, En1 and Fgf8 in specification and regionalisation of the midbrain. *Development* 126, 945-59.

Sheikh, H., and Mason, I. (1996). Polarising activity of FGF-8 in the avian midbrain. *Int J Dev Biol* Suppl, 117S-118S.

Si, Z., Amendt, B. A., and Stolzfus, C. M. (1997). Splicing efficiency of huamn immunodeficiency virus type 1 tat RNA is determined by both a suboptimal 3' splice site and a 10 nucleotide exon splicing silencer element located with tat exon 2. *Nucleic Acids Reseach* 25, 861-867.

Simons, R. W. (1993). The control of prokayotic and eukaryotic gene expression by antturally occurring antisense RNA. In "Antisense Research and Applications" (S. T. a. L. Crooke, B., Ed.), pp. 97-124. CRC Press Inc., Boca Raton.

Siomi, H., and Dreyfuss, G. (1995). A nuclear localization domain in the hnRNP A1 protein. *J Cell Biol* 129, 551-60.

Siomi, H., and Dreyfuss, G. (1997). RNA-binding proteins as regulators of gene expression. *Curr Opin Genet Dev* 7, 345-53.

Siomi, M. C., Eder, P. S., Kataoka, N., Wan, L., Liu, Q., and Dreyfuss, G. (1997). Transportin-mediated nuclear import of heterogeneous nuclear RNP proteins. *J Cell Biol* 138, 1181-92.

Siomi, M. C., Fromont, M., Rain, J. C., Wan, L., Wang, F., Legrain, P., and Dreyfuss, G. (1998). Functional conservation of the transportin nuclear import pathway in divergent organisms. *Mol Cell Biol* 18, 4141-8.

Slack, J. M., Darlington, B. G., Heath, J. K., and Godsave, S. F. (1987). Mesoderm induction in early Xenopus embryos by heparin-binding growth factors. *Nature* 326, 197-200.

Sommer, B., Kohler, M., Sprengel, R., and Seeburg, P. H. (1991). RNA editing in brain controls a determinant of ion flow in glutamate-gated channels. *Cell* 67, 11-9.

Stade, K., Ford, C. S., Guthrie, C., and Weis, K. (1997). Exportin 1 (Crm1p) is an essential nuclear export factor. *Cell* 90, 1041-50.

Steitz, J. A., Black, D. L., Gerke, V., Parker, K. A., Dramer, A., et al. (1988). . In "Structure and function of Major and Minor Small Nuclear Ribonucleoproteins" (M. L. Birnsteil, Ed.), pp. 115-154. SpringerNerlag, Berlin/New York.

Stolt, P., and Zillig, W. (1993). Antisense RNA mediates transcriptional processing in an archaebacterium, indicating a novel kind of RNase activity. *Mol Microbiol* 7, 875-82.

Storey, K. G., Goriely, A., Sargent, C. M., Brown, J. M., Burns, H. D., Abud, H. M., and Heath, J. K. (1998). Early posterior neural tissue is induced by FGF in the chick embryo. *Development* 125, 473-84.

Sweet, D. J., and Gerace, L. (1996). A GTPase distinct from Ran is involved in nuclear protein import. *J Cell Biol* 133, 971-83.

Szebenyi, G., and Fallon, J. F. (1999). Fibroblast growth factors as multifunctional signaling factors. *Int Rev Cytol* 185, 45-106.

Szebenyi, G., Savage, M. P., Olwin, B. B., and Fallon, J. F. (1995). Changes in the expression of fibroblast growth factor receptors mark distinct stages of chondrogenesis in vitro and during chick limb skeletal patterning. *Dev. Dyn.* 204, 446-456.

Tempst, P., Link, A. J., Riviere, L. R., Fleming, M., and Elicone, C. (1990). Internal sequence analysis of proteins separated on polyacrylamide gels at the submicrogram level: improved methods, applications and gene cloning strategies. *Electrophoresis*. 11, 537-553.

Tolnay, M., Lambris, J. D., and Tsokos, G. C. (1997). Transcriptional regulation of the complement receptor 2 gene: role of a heterogeneous nuclear ribonucleoprotein. *J Immunol* 159, 5492-501.

Tolnay, M., Vereshchagina, L. A., and Tsokos, G. C. (1999). Heterogeneous nuclear ribonucleoprotein DOB is a sequence-specific DNA-binding protein. *Biochem J* 338, 417-25.

Tomasek, J. J., Mazurkiewicz, J. E., and Newman, S. A. (1982). Nonuniform distribution of fibronectin during avian limb development. *Dev. Biol*. 90, 118-126.

Truant, R., Fridell, R. A., Benson, R. E., Bogerd, H., and Cullen, B. R. (1998). Identification and functional characterization of a novel nuclear localization signal present in the yeast Nab2 poly(A)+ RNA binding protein. *Mol Cell Biol* 18,1449-58.

Valcarcel, J., Singh, R., Zamore, P. D., and Green, M. R. (1993). The protein Sex-lethal antagonizes the splicing factor U2AF to regulate alternative splicing of transformer pre-mRNA. *Nature* 362, 171-5.

Van Obberghen-Schilling, E., Roche, N. S., Flanders, K. C., Sporn, M. B., and Roberts, A. (1988). Transforming growth factor beta-1 positively regulates its own expression in normal and transformed cells. *J. Biol. Chem*. 263, 7741-7746.

Vanhee-Brossollet, C., Thoreau, H., Serpente, N., D'Auriol, L., Levy, J. P., and Vaquero, C. (1995). A natural antisense RNA derived from the HIV-1 env gene encodes a protein which is recognized by circulating antibodies of HIV+ individuals. *Virology* 206, 196-202.

Vanhee-Brossollet, C., and Vaquero, C. (1998). Do natural antisense transcripts make sense in eukaryotes? *Gene* 211, 1-9.

Voelker, R. A., Graves, J., Gibson, W., and Eisenberg, M. (1990). Mobile element insertions causing mutations in the Drosophila suppressor of sable locus occur in DNase I hypersensitive subregions of 5'-transcribed nontranslated sequences. *Genetics* 126, 1071-82.

Vogel, A., Rodriguez, C., and Izpisua-Belmonte, J. C. (1996). Involvement of FGF-8 in initiation, outgrowth and patterning of the vertebrate limb. *Development* 122, 1737-1750.

Von Besser, H., Schnabel, P., Wieland, C., Fritz, E., Stanwsky, R., et al. (1990). *Chromosoma* 100, 37-47.

Wagner, E. G., and Simons, R. W. (1994). Antisense RNA control in bacteria, phages, and plasmids. *Annu Rev Microbiol* 48, 713-42.

Walicke, P., Cowan, W. M., Ueno, N., Baird, A., and Guillemin, R. (1986). Fibroblast growth factor promotes survival of dissociated hippocampal neurons and enhances neurite extension. *Proc Natl Acad Sci U S A* 83, 3012-6.

Walshe, J., and Mason, I. (2000). Expression of FGFR1, FGFR2 and FGFR3 during early neural development in the chick embryo. *Mech Dev* 90, 103-10.

Wang, J., and Manley, J. L. (1997). Regulation of pre-mRNA splicing in metazoa. *Curr Opin Genet Dev* 7, 205-11.

Wang, J., Xiao, S. H., and Manley, J. L. (1998). Genetic analysis of the SR protein ASF/SF2: interchangeability of RS domains and negative control of splicing. *Genes Dev* 12, 2222-33.

Watanabe, A., and Ide, H. (1993). Basic FGF maintains some characteristics of the progress zone of chick limb bud in cell culture. *Dev Biol* 159, 223-31.

Wedeen, C. J., and Figueroa, N. B. (1998). Expression of actin mRNA in embryos of the leech *Helobdella triserialis*. *Int J Dev Biol* 42, 581-90.

Weighardt, F., Biamonti, G., and Riva, S. (1995). Nucleo-cytoplasmic distribution of human hnRNP proteins: a search for the targeting domains in hnRNP A1. *J Cell Sci* 108, 545-55.

Weighardt, F., Biamonti, G., and Riva, S. (1996). The roles of heterogeneous nuclear ribonucleoproteins (hnRNP) in RNA metabolism. *Bioessays* 18, 747-56.

Weis, K. (1998). Importins and exporting: how to get in and out of the nucleus [published erratum appears in Trends Biochem Sci 1998 Jul;23(7):235]. *Trends Biochem Sci* 23, 185-9.

Weis, K., Ryder, U., and Lamond, A. I. (1996). The conserved amino-terminal domain of hSRP1 alpha is essential for nuclear protein import. *Embo J* 15, 1818-25.

Wen, W., Harootunian, A. T., Adams, S. R., Feramisco, J., Tsien, R. Y., Meinkoth, J. L., and Taylor, S. S. (1994). Heat-stable inhibitors of cAMP-dependent protein kinase carry a nuclear export signal. *J Biol Chem* 269, 32214-20.

Wilke, T. A., Gubbels, S., Schwartz, J., and Richman, J. M. (1997). Expression of fibroblast growth factor receptors (FGFR1, FGFR2, FGFR3) in the developing head and face. *Dev Dyn* 210, 41-52.

Wilkie, A. O., Slaney, S. F., Oldridge, M., Poole, M. D., Ashworth, G. J., Hockley, A. D., Hayward, R. D., David, D. J., Pulleyn, L. J., Rutland, P., and et al. (1995). Apert syndrome results from localized mutations of FGFR2 and is allelic with Crouzon syndrome [see comments]. *Nat Genet* 9, 165-72.

Yamada, K. M., and Kennedy, D. W. (1985). Amino acid sequence specificities of an adhesive recognition signal. *J Cell Biochem* 28, 99-104.

Yang, Q., Rout, M. P., and Akey, C. W. (1998). Three-dimensional architecture of the isolated yeast nuclear pore complex: functional and evolutionary implications. *Molecular Cell* 1, 223-234.

Yang, X., Bani, M. R., Lu, S. J., Rowan, S., Ben-David, Y., and Chabot, B. (1994). The A1 and A1B proteins of heterogeneous nuclear ribonucleoparticles modulate 5' splice site selection in vivo. *Proc Natl Acad Sci U S A* 91, 6924-8.

Yayon, A., Zimmer, Y., Shen, G. H., Avivi, A., Yarden, Y., and Givol, D. (1992). A confined variable region confers ligand specificity on fibroblast growth factor receptors: implications for the origin of the immunoglobulin fold. *Embo J* 11, 1885-90.

Yoshida, T., Kokura, K., Makino, Y., Ossipow, V., and Tamura, T. A. (1999). Heterogeneous nuclear RNA-ribonucleoprotein F binds to DNA via an oligo(dG)-motif and is associated with RNA polymerase II. *Genes Cells* 4, 707-719.

Zahler, A. M., Neugebauer, K. M., Lane, W. S., and Roth, M. B. (1993). Distinct functions of SR proteins in alternative pre-mRNA splicing. *Science* 260, 219-22.

Zhang, Q. (1995). Characterization of the nuclear cAMP signalling pathway during limb cartilage differentiation. In "Cell Biology and Anatomy", pp. 126. New York Medical College, Valhalla, N.Y.

Zhang, Q., Carr, D. W., Lerea, K. M., Scott, J. D., and Newman, S. A. (1996). Nuclear localization of type II cAMP-dependent protein kinase during limb cartilage differentiation is associated with a novel developmentally-regulated A-kinase anchoring protein. *Developmental Biology* 176, 51-61.

Zhu, X., Sasse, J., and Lough, J. (1999). Evidence that FGF receptor signaling is necessary for endoderm-regulated development of precardiac mesoderm. *Mech Ageing Dev* 108, 77-85.

Zieve, G. W., and Sauterer, R. A. (1990). Cell biology of the snRNP particles. *Crit Rev Biochem Mol Biol* 25, 1-46.

BACKGROUND OF THE INVENTION

The spatial and temporal coordination of gene expression during embryogenesis involves a variety of regulatory mechanisms, of which those acting at the transcriptional level have been most intensively studied (Davidson et al., 1998; Gellon and McGinnis, 1998; Gray and Levine, 1996; Mannervik et al., 1999). Less is known about mechanisms that control differential production and accumulation of specific proteins at various sites in the developing embryo at the post-transcriptional level, causing the RNA transcript to be spliced appropriately, or regulating transport of the spliced mRNA to the cytoplasm. Recent interest in the role of differential splicing in development and the factors and mechanisms by which it is accomplished (Chabot, 1996; Lopez, 1998), and a growing understanding of the determinants of nucleo-cytoplasmic transport of particular mRNAs (Piñol-Roma and Dreyfuss, 1992; Siomi and Dreyfuss, 1997; Weis, 1998), has set the stage for a systematic analysis of how these RNA processing factors contribute to regional and cell type specificity in the embryo.

The ribonucleoprotein hnRNP A1 is of particular interest in this regard, as it functions in both RNA splice site selection and nucleus-to-cytoplasm transport of mRNA. In its capacity as a splicing factor, this protein modulates 5' splice site selection in a group of gene products, some of which contain a well-characterized RNA sequence determinant (Burd and Dreyfuss, 1994). Among these are the pre-mRNAs of the HIV type 1 tat protein (Del Gatto-Konczak et al., 1999), FGF receptor 2 (FGFR2) (Del Gatto-Konczak et al., 1999), and hnRNP A1 itself (Chabot et al., 1997). In its role in nucleus-to-cytoplasm transport, hnRNP A1 acts as a "shuttle" protein (Piñol-Roma and Dreyfuss, 1992), and is characterized by a novel amino acid motif termed M9, which contains both nuclear localization and nuclear export activities (Michael et al., 1995; Siomi and Dreyfuss, 1995).

The known functions of hnRNP A1 as an RNA shuttle protein and in splice choice selection are exerted in a gene product-specific fashion (Dreyfuss et al., 1993). The tissue-restricted spatiotemporal patterns in the protein's expression reported are therefore likely to be a causal component of the process by which cell types become distinctive from one another during organogenesis. A subclass of primary transcripts (including hnRNP A1 itself, Chabot et al., 1997; Mayeda et al., 1994) is differentially spliced by a process that depends on hnRNP A1. Control of splice choice appears to involve the antagonism of constitutive splicing factors such as SF2/ASF by members of the hnRNP A/B family of proteins (Mayeda and Krainer, 1992, Mayeda et al., 1993, 1994; Del Gatto-Konczak et al., 1999). Once spliced, these RNAs are transported into the cytoplasm by a process that involves hnRNP A1 and transportin 1 (Nakielny and Dreyfuss, 1998, Nakielny et al., 1999). This implies that the regulation of hnRNP A1 levels within living cells during development plays a key role in cell type diversification.

Earlier studies have surveyed the distribution of hnRNP A1 in a limited set of adult cell types (Kamma et al., 1995; Faura et al., 1995) including the developing germ cells of postnatal mice. A study by the inventors and their colleagues documenting the characterization of the sequence of chicken hnRNP A1 and its spatiotemporal and organ-specific expression during embryogenesis is hereby incorporated by reference in its entirety. (Bronstein et al., 2001). hnRNP A1 protein is abundantly expressed in early stage epithelia such as skin, extraembryonic membranes, and neuroectoderm; epithelioid tissues, such as liver; as well as "secondary" epithelia and epithelioid tissues derived from mesenchymes, e.g., heart muscle, skeletal muscle, kidney tubules, sinusoidal vascular endothelium, and precartilage condensations. It is not clear, however whether this pattern represents an authentic expression theme, or simply the prevalence both of epithelioid tissues in the early embryo and of hnRNP A1 expression. (Bronstein et al., 2001).

The expression of hnRNP A1 in differentiating neuroectoderm and dorsal root ganglia broadly coincides with patterns of expression of members of the Hu class of RNA binding protein genes in the chicken (Wakamatsu and Weston, 1997) and it is significant in this regard that the Hu family of proteins results from extensive alternative splicing of Hu gene products during neurogenesis (Okano and Darnell, 1997). However, while the expression of the two RNA binding proteins may be partly overlapping, they are not entirely so: the typical DRG cell nuclei expressing hnRNP A1 are larger than those expressing Hu and vertebral body cartilage expresses hnRNP A1 but not Hu.

The transcription of natural antisense RNA cognate to exonic sequences of the hnRNP A1 gene in many of the same tissues that are producing sense transcript is an unusual phenomenon, but one that is not as rare as previously thought (Dolnick, 1997; Vanhee-Brossollet and Vaquero, 1998). Antisense RNA probably functions as a post-transcriptional inhibitor of gene expression (Knee and Murphy, 1997). This regulatory mechanism may be particularly relevant during development—natural antisense transcripts of several developmentally active growth factors—fibroblast growth factor-2 (Savage and Fallon, 1995), bone morphogenetic protein-2 (Feng et al., 1997), and transforming growth factor-2 (Coker et al., 1998)—have been detected at significant levels, the first two in embryonic tissues. There is one previous report of differential expression of natural antisense RNA expression of a splicing factor gene (Sureau et al., 1997). Moreover, since hnRNP A1 can promote RNA-RNA strand annealing (Cobianchi et al., 1993; Idriss et al., 1994) it is itself a potential component of natural antisense regulatory mechanisms (Oberosler and Nellen, 1997).

The organ- and tissue-specific sense and antisense hnRNP A1 RNA expression patterns seen at different stages are consistent with the idea that antisense expression may be playing a regulatory role during development. For example, in kidney and liver virtually all cells at the early stages express the sense transcript. But whereas the protein product is also broadly distributed in liver the more limited distribution of the protein in kidney may be related to the more localized distribution of antisense RNA during development of this organ.

Because hnRNP A1 helps regulate nuclear-cytoplasmic transport and alternative splicing for well-defined classes of transcripts, its own regulation can provide the basis for post-transcriptional control of the partitioning of organ primordia into distinct gene expression domains. It is therefore significant that the hnRNP A1 gene is widely transcribed throughout the early embryo and its encoded protein is subject to numerous demonstrated and potential autoregulatory effects at the post-transcriptional level: it helps splice its own pre-mRNA, it may transport its own mRNA from the nucleus to the cytoplasm, and it may participate in the regulation of its own synthesis by its gene's antisense transcript. Small changes in the balance of any of these processes, or of other possible but speculative ones, such as unmasking of maternally inherited hnRNP A1, or even transfer of the protein from one cell to another, could thus activate a post-transcriptional cascade leading to the local expression of hnRNP A1, and with it the expression of its target gene products.

The recent recognition that a large proportion of the genes constituting the human genome are alternatively spliced (Ewing and Green, 2000) (a recent estimate indicates that 38% of human mRNAs contain possible alternative splice forms; Bretta et al., 2000) highlights the centrality of the developmental regulation of hnRNP A1 and other nonconstitutive splicing factors in the generation of complexity in vertebrate organisms.

Classes of hnRNP Proteins

In eukaryotes, heterogeneous nuclear RNAs (hnRNAs), which are the products of RNA polymerase II, are extensively processed to produce messenger RNAs (mRNAs). mRNA processing includes capping, splicing, and polyadenylation (Dreyfuss et al., 1993) and involves the association of the hnRNAs with nuclear proteins collectively known as ribonucleoprotein (RNP) complexes (Dreyfuss et al., 1993; Michael et al., 1995). RNPs that directly bind to hnRNAs are classified as the hnRNPs and are involved in the splicing and shuttling of pre-mRNAs. Others are categorized into special classes such as small nuclear ribonuclear proteins (snRNPs) and include the U snRNPs (Bandziulis et al., 1989; Dreyfuss et al., 1993; Dreyfuss et al., 1988; Luhrmann, 1990; Steitz, 1988; Zieve and Sauterer, 1990). The mature transcript produced from the hnRNA-hnRNP-snRNP complex is transported to the cytoplasm by specific hnRNPs where it may associate with yet another set of RNPs involved in translational regulation and mRNA stability (Bandziulis et al., 1989; Dreyfuss et al., 1993; Luhrmann, 1990; Steitz, 1988; Zieve and Sauterer, 1990).

hnRNP proteins are highly conserved throughout the vertebrates, as well as having sequence homologies in the invertebrate *Drosophila* (Amrein et al., 1988; Robinow and White, 1988) (Bell et at., 1991; Dreyfuss et at., 1993; Inoue et at., 1990; Kay et at., 1990; Roth et al., 1991; Voelker et al., 1990; Von Besser, 1990), and are the most abundant proteins found in the nucleus (Dreyfuss, 1986, Dreyfuss, 1993). In HeLa cells two-dimendional gel electrophoresis has resolved 20 major groups of proteins. These proteins are designated as the heterogeneous nuclear ribonucleoproteins (hnRNPs) A1 (~34 kDa) to hnRNP U (~120 kDa), and categorized by structural motifs (Cobianchi, 1990; Dreyfuss et al., 1993; Matunis et al., 1992; Pinol-Roma et at., 1988). Furthermore, sequence analysis has determined that hnRNPs have one or more RNA-binding modules referred to as the RNP motif or RNA Recognition Motif (RRM) in addition to at least one other auxiliary domain (Dreyfuss et al., 1993). The RNP motif contains two consensus sequences, RNP1 and RNP2, within a domain of approximately 90 amino acid residues that are located about 30 amino acids from each other (Dreyfuss et al., 1993; Dreyfuss et al., 1988). The RNP 1 module is an octapeptide, Lys/Arg-Gly-Phe/Tyr-Gly/Ala-Phe-Val-X-Phen/Tyr, SEQ ID NO: 7 in the Sequence Listing (Adam et al., 1986; Dreyfuss et al., 1993), while the RNP2 module is a hexapeptide rich in aromatic and aliphatic amino acids and is less well conserved (Dreyfuss et al., 1993; Dreyfuss et al., 1988). Both of these consensus sequences are directly related to RNA binding (Dreyfuss et al., 1993; Merrill et al., 1988).

Functional and structural categories of human hnRNPs include:

(i) hn RNP A2/B1 complexes with the snRNPs and plays a role in splicing pre-mRNAs. Though localized in the nucleus of most tissues, A2 is also found in the cytoplasm of the squamous epithelium of the skin and the esophagus, and abundant amounts of A2 are found in the medulla, but not the cortex of the adrenal gland. Both A2 and B1 are found throughout spermatogenesis while A1 expression is repressed in spermatocytes (Kamma et al., 1999).

(ii) hnRNP C1 is involved in the post-translation base change of cytosine to uracil in the apolipoprotein (apo) B mRNA which codes for the catalytic subunit APOBEC-1, a protein involved in splicesome assembly. C1 may regulate apoB mRNA editing thus restricting the activity of the catalytic subunit (Greeve et al., 1998).

(iii) hnRNP D is involved in the immunoglobulin heavy chain recombination process by binding to the switching regions in conjunction with a B cell-specific duplex DNA binding factor (Dempsey et al., 1999), while transcriptional regulation of the complement receptor 2 (CR2) is achieved by hnRNP DOB through its binding of both single and double stranded DNA (Tolnay et al., 1997; Tolnay et al., 1999).

(iv) hnRNP K may play a role in cytosine-rich pre-mRNA metabolism and cell cycle progression. Highly upregulated levels of K have been found in transformed keratinocytes (Dejgaard et al., 1994).

(v) hnRNP H, H' are posttranslationally cleaved to produce the C-terminal proteins H(C) and H(C') both having a molecular weight of 35 kDa with localization primarily in the nucleus. In contrast, hnRNP F varies with its localization depending on the cell type and is predominantly cytoplasmic in some cells which may be important its function (Honore et al., 1999).

(vi) Autoantibodies of hnRNP A1, A2, B have been found in individuals with connective tissue diseases. In addition to the A/B proteins, hnRNP I has been found in patients with systemic sclerosis (SSc) and in particular, in individuals with pre-SSc or limited SSc. The A/B and I protein complexes may elicit autoimmune responses (Montecucco et al., 1996).

(vii) The hnRNP L protein, having an unknown function, is found both as a component of the hnRNP complex as well as in discrete nonnucleolar structures of the nucleoplasm in HeLa cells (Pinol-Roma et al., 1989).

(viii) Finally hnRNP R, an hnRNP P-like protein, was isolated from yet another individual with autoimmune symptoms and may be a component of subcellular particles that are found in autoimmune diseases (Hassfeld et al., 1998). This protein may have some relationship to the gene product of the TLS/FUS gene, an RNA binding protein identical to hnRNP P2, and first identified as a fusion protein in human myxoid liposarcomas (Calvio et al., 1995; Crozat et al., 1993; Hassfeld et al., 1998; Rabbitts et al., 1993).

In addition, the hnRNP classes of RNA-binding proteins have been shown to be developmentally important in many embryonic tissues including the formation and maintenance of the nervous system (Dreyfuss et al., 1993), sex determination in *Drosophila melanogaster* (Bandziulis et al., 1989; Del Gatto-Konczak et al., 1999; Lynch and Maniatis, 1995; Lynch and Maniatis, 1996), neuronal splice activation (Del Gatto-Konczak et al., 1999; Min, 1997) and maintenance (Dreyfuss, 1993), and epithelial/mesenchymal differentiation (Johnson and Williams, 1993). In Drosophila, the embryonic lethal abnormal visual (ELAV) system proteins are required for correct differentiation and maintenance of neurons. In mammals the ELAV-like neuronal RNA-binding proteins HuB, HuC, and HuD are implicated in neuronal development and differentiation in both the central and peripheral nervous systems (Akamatsu et al., 1999; Kasashima et al., 1999). In other systems such as the human immunodeficiency virus (HIV-1) hnRNPs are involved in regulating exon 2 of the tat splicing gene (Del Gatto-Konczak et al., 1999; Si, 1997).

hnRNP A1

The hnRNP A1 protein contains two RNP consensus motifs, a glycine-rich auxiliary domain at its carboxy-terminus (Burd and Dreyfuss, 1994; Burd et al., 1989; Buvoli et al., 1990; Merrill et al., 1988), as well as an RGG box, also at its carboxy-terminus (Kiledjian and Dreyfuss, 1992). In addition to these motifs, the hnRNP A1 class of proteins contain a nuclear localization signal, within a domain of approximately 38 amino acids at the carboxy-terminal region of the protein (Michael et al., 1995). This motif, referred to as M9, is a novel nuclear localization signal (NLS)/nuclear export signal (NES) and is not homologous to the classical nuclear localization signal (NLS) found, for example in either the large T antigen of the SV40 virus or the bipartite basic NLS of nucleoplasmin (Izaurralde et al., 1997b; Kalderon et al., 1984; Michael et al., 1995; Robbins et al., 1991; Weighardt et al., 1995). The presence of the M9 motif allows hnRNPs to shuttle continuously between the nucleus and the cytoplasm (Dreyfuss et al., 1993). hnRNPs of the A1, A2/B1, D, E, I and K classes have this capability, while those of the C1, C2, and U class are found restricted to the nucleus (Izaurralde et al., 1997b; Michael et al., 1995; Pinol-Roma and Dreyfuss, 1992). Furthermore, hnRNP A1 is found bound to the poly $(A)^+$ tail of RNA polymerase II transcripts in both the nucleus and the cytoplasm and data suggest that the hnRNP A1 protein is transported out of the nucleus with the mature message during the export process (Pinol-Roma and Dreyfuss, 1992).

FIG. 1a shows the cDNA sequence designated SEQ ID NO:1 and FIG. 1b shows the amino acid sequence of chicken hnRNP A1 (indicated by CHKA1) designated SEQ ID NO:2 compared to the human hnRNP A1 amino acid sequence (indicated by HUMA1) designated SEQ ID NO:3.

FIG. 2 illustrates the structure of the human core hnRNP proteins A1, A1.sup.B, A2 and B1. The RNP-2 and RNP-1 conserved submotifs of RRM1 and RRM2, and the G domains of each protein are shown. hnRNP A1 (SEQ ID NO. 8) and A1.sup.B or hnRNP A2 (SEQ ID NO. 9) and B1 (SEQ ID NO. 10) are identical except for extra amino acid regions indicated by boxes. The sequences of the RNP-1 and RNP-2 submotifs are aligned. The dots in the alignment indicate amino acid identities. All recombinant proteins are in authentic form except for post-translational modifications. The numbers indicate the position of amino acid residues from the initiation codon Met1. Based on published cDNA sequences (Burd, 1989; Buvoli, 1990). After Mayeda et al. (1994).

hnRNP A1 and Splice Choices

In a multi-step process, uracil rich small nuclear ribonuclear proteins (U snRNPs) in association with the core hnRNPs A1, A2, B1, B2, C1, C2, and C3 (classified by increasing molecular weight), bind to the pre-mRNAs in an ordered manner at specific sequences forming the spliceosome (Beyer et al., 1977; Chung and Wooley, 1986; Del Gatto, 1996; Dreyfuss, 1986; Kumar et al., 1986; Mayeda and Krainer, 1992). Alternative splicing allows for the functional and structural diversity of gene products by the addition or deletion of elements as small as a single amino acid (as seen in the Pax-3 and Pax-7 gene products) (Lopez, 1998). Additional means of obtaining protein variants from a single transcript in a cell-specific manner include splice activation and splice repression (Del Gatto-Konczak et al., 1999).

Alternative splicing may involve the use of alternative 5' or 3' splice sites, optional exons, exclusive exons, or retained introns (Lopez, 1998). Except for intron retention, splicing patterns are under competitive control of splicing proteins (Lopez, 1998). Splice activation may involve multi-protein complexes on pre-mRNAs. An example of this is seen in the activation of the female specific dsx exon of *Drosophila melanogaster* by the female specific proteins, tra (transformer), tra-2 and SR (splice regulator proteins rich in arginine/glycine repeats) (Del Gatto-Konczak et al., 1999; Lynch and Maniatis, 1995; Lynch and Maniatis, 1996; Wang et al., 1998). In the mouse, the c-scr exon N1 is activated by the KSRP splicing factor (KH-type splicing regulator) (Min, 1997; Wang and Manley, 1997) which induces the assembly of five other proteins including hnRNP F (a pre-mRNA splicing factor which is associated with the TATA-binding protein, essential for transcription initiation (Del Gatto-Konczak et al., 1999; Min, 1997; Yoshida et al., 1999). This multiprotein complex activates the intronic splicing enhancer that splices the neuronal specific c-scr N1 exon in vitro (Del Gatto-Konczak et al., 1999; Min, 1997).

Splice repression involves protein binding to an intronic 3' splice site and is seen in the female-specific Sxl protein of *Drosophila*. This interaction effectively blocks U2 snRNP and U2AF (U2 snRNP auxiliary factor) (Del Gatto, 1996; Del Gatto-Konczak et al., 1999; Lopez, 1998; Valcarcel et al., 1993). Other protein complexes may use exon sequences for splice repression.

Vertebrate genes including the human fibroblast growth factor receptor 2 gene (fgfr2), and the human immunodeficiency virus type 1 (HIV-1) tat gene contain exons that have sequences acting as exonic splice silencers (ESS) (Amendt et al., 1994; Amendt et al., 1995; Baba-Aissa et al., 1998; Caputi et al., 1994; Caputi et al., 1999; Del Gatto, 1995; Del Gatto, 1996; Del Gatto-Konczak et al., 1999; Gallego et al., 1996; Graham et al., 1992; Si, 1997).

The ESS of the human FGFR2 pre-mRNA contains a UAGG sequence in the kgfr exon (keratinocyte growth factor receptor-exon 8)(Del Gatto, 1996; Del Gatto and Breathnach, 1995; Del Gatto-Konczak et al., 1999). This sequence has homology to the high affinity consensus sequence 5'-UAGGGA/U-3' recognized by hnRNP A1 (Del Gatto-Konczak et al., 1999). In in vitro studies, Del Gatto-Konczak et al. (1999) have demonstrated that hnRNP A1 can modulate splice choices by binding to a 10 mer ESS designated S10 (5'-UAGGGCAGGC-3', SEQ ID NO: 5 in the Sequence Listing) or to a 6 mer ESS designated S6 (5'-UAGGGC-3').

In in vitro studies, RNA molecules containing the splicing silencer sequence from the human fibroblast receptor 2 kgfr exon (IIIb) were capable of directing splice choice selection by the recruitment hnRNP A1 (Del Gatto-Konczak et al., 1999). When the following point mutations were introduced into the S6 ESS UCGGGC or UACGGC a two-fold decrease in hnRNP A1 binding was detected (Del Gatto-Konczak et al., 1999). Furthermore, it was determined that the targeting of hnRNP A1 to the ESS domain was through the glycine-rich motif at the C-terminus of the protein. In the human hnRNP A1 protein, the glycine-rich domains are found between residues 189-320: the RGG motif is specifically located at residues 189-247, followed by another glycine-rich motif from residues 239-320 (Del Gatto-Konczak et al., 1999). Silencing of the k-sam (kgfr) exon in these in vitro studies required the entire glycine-rich motif By examining the corresponding sequence in the chicken kgfr exon (IIIb exon 8) of fgfr2 it has been determined that the sequence corresponding to the human ESS is 5'-UAGGGAGGGC-3', SEQ ID NO: 6 in the Sequence Listing).

Studies involving hnRNP A1 proteins demonstrated that it is capable of promoting RNA molecules to base pair into double stranded structures, therefore influencing pre-mRNA splicing by snRNPs (Burd and Dreyfuss, 1994; Buvoli et al., 1992; Eperon et al., 1993; Kumar and Wilson, 1990; Munroe and Dong, 1992; Pontius and Berg, 1990; Portman and Dreyfuss, 1994). In in vitro assays hnRNP A1, as well as the RNA binding protein splicing factor 2 (ASF/SF2) (a member of the SR nuclear phosphoprotein family) were capable of making splice choices at the 5' splice site of pre-mRNAs that contain multiple 5' splice sites and are essential for constitutive splicing (Caceres et al., 1997; Caceres et al., 1998; Del Gatto, 1996; Fu, 1995; Ge and Manley, 1990; Krainer et al., 1990; Manley and Tacke, 1996; Mayeda et al., 1993; Mayeda and Krainer, 1992; Mayeda et al., 1994; Munroe and Dong, 1992; Zahler et al., 1993).

In vitro studies suggest that hnRNP A1 and ASF/SF2 may act antagonistically and that the hnRNP A/B family of splicing proteins regulates the SR family both in vitro and in vivo (Caceres et al., 1998; Caceres et al., 1994; Mayeda and Krainer, 1992; Yang et al., 1994). In in vitro experiments, excess hnRNP A1 favored the distal 5' splice site, in contrast to excess ASF/SF2 favoring proximal 5' splice sites in a concentration-dependent manner resulting in alternate splicing patterns of many genes in specific cell types (Del Gatto, 1996; Mayeda et al., 1993; Mayeda and Krainer, 1992; Mayeda et al., 1994; Munroe and Dong, 1992). Burd and Dreyfuss (1994) have shown that the consensus sequence 5'-UAGGGA/U-3' is a high affinity binding site of hnRNP A1 and that this sequence is similar to the 5' and 3' splice sites in vertebrate pre-mRNAs. In addition, the ability of hnRNP A1 to bind to this consensus sequence increased if it was duplicated and separated by two nucleotides, resulting in a dissociation constant of $1 \times 10^{-9}$ M. While hnRNP A1 proteins are capable of binding to other pre-mRNA sites, binding affinity varies greatly over a >100 fold range, therefore classifying these proteins as sequence specific RNA binding proteins (Burd and Dreyfuss, 1994).

hnRNP A1 is also involved in self-splicing. The 4.6 kb human hnRNP A1 mRNA containing 10 exons encodes for the 34 kDa hnRNP A1 protein. The pre-mRNA for hnRNP A1 can be differentially spliced to produce the A1 form and $A1^B$ form (Buvoli et al., 1990). It has been shown that the human hnRNP $A1^B$ protein (FIG. 2) with an apparent molecular weight of 38 kDa, corresponds to the protein previous designated as hnRNP B2 (Buvoli et al., 1990). The $A1^B$ splice variant which contains an extra exon in the C-terminal region glycine-rich region (156 bp; 52 amino acids) has a higher affinity for ssDNA than the 34 kDa form though its abundance in the cell is only ~5% that of hnRNP A1 (Buvoli et al., 1990).

More recently, Blanchette and Chabot (1997) have shown that alternative splicing of the hnRNP A1 pre-mRNA yields the A1 and $A1^B$ forms via 5' splice selection and exon skipping, and that this process requires conserved elements. Studies have shown that the addition of the alternate exon 7B in the mature mRNA produces the hnRNP $A1^B$ protein (Buvoli et al., 1990). Furthermore, Blanchette and Chabot have demonstrated that the conserved intron element (CE1) upstream from exon 7B favors distal 5' splice site selection. SR proteins, including SF2, which favor the proximal 5' splice selection site, require U1 snRNP and U2AF when involved in the 5' splice site stimulation of a 3' splice site, as seen in the male specific 3' splice site of tra in *Drosophila* (Blanchette and Chabot, 1997; Valcarcel et al., 1993). Interestingly, the CE1 element does not interfere with U1 snRNP binding and led to the discovery of an additional element CE610, which is located downstream from exon 7B. CE610 is also involved in distal 5' splice site selection by secondary structure formation and exon skipping (Blanchette and Chabot, 1997). Since the SR family of splice selection proteins and hnRNP A1 act antagonistically for 5' splice choices, where the SRs choose the 5' proximal site and the hnRNPs the 5' distal site (Weighardt et al., 1996), hnRNP A1 may be involved in modulating its own splicing (Blanchette and Chabot, 1997; Chabot et al., 1997; Del Gatto-Konczak et al., 1999; Mayeda et al, 1994).

Fibroblast Growth Factors (FGFs), Fibroblast Growth Factor Receptors (FGFRs), and FGFR-2 Splice Variants Fibroblast growth factors (FGFs) are important mitogens in both cell proliferation and differentiation, but in some cases may act as antagonists and inhibit differentiation. Examples of FGF induced differentiation are seen in the stimulation of pre-adipocyte fibroblasts (Broad and Ham, 1983; Johnson and Williams, 1993; Serrero and Khoo, 1982), and hippocampal neurite outgrowth (Johnson and Williams, 1993; Walicke et al., 1986). Developmental roles have been demonstrated in embryonic mesodermal induction in Xenopus (Kimelman and Kirschner, 1987; Slack et al., 1987), and the inhibition of differentiation of myotubes has been shown in skeletal muscle (Linkhart et al., 1981). In addition to acidic FGF (aFGF or FGF1) and basic FGF (bFGF or FGF2), the family of FGFs, including keratinocyte growth factor (KGF) have been shown to stimulate the proliferation of mesenchymal and neuroectodermal cell types (Burgess and Maciag, 1989; Johnson and Williams, 1993). Using immunohistochemical analysis on chick embryo sections, FGF2 has been localized to the heart, myotome, limbs and muscles (Han, 1997; Joseph-Silverstein, 1989) as well as to the notochord, neural tissue, gut cells, and tubules in the mesonephric and metanephric kidneys (Dono and Zeller, 1994; Han, 1997). In addition to the previously mentioned tissues, Han (1997) localized this mitogen to the developing pharyngeal arches, specifically the maxilla and mandible. FGF2 plays an important role in morphogenesis and pattern formation in the vertebrate limb (Han, 1997; Noji et al., 1993; Riley et al., 1993; Savage et al., 1993), as well as in kidney development (Dono and Zeller, 1994; Han, 1997).

Receptors for the 19 known fibroblast growth factors (FGFs) (Hu et al., 1998; Ohbayashi et al., 1998) include the tyrosine kinase fibroblast growth factor receptors (FGFRs) (Johnson and Williams, 1993), the CFR receptor or cytosine rich FGFR, (Burrus and Olwin, 1989) and the heparan sulfate proteoglycans (HSPGs). In chicken, the genes for fgfrs1, 2, and 3 and 4 (fgfr-related kinase or frek) as well as the kgfr (exon IIIb-keratinocyte growth factor receptor) and bek (exon IIIc-bacterial expressed kinase) splice variants for receptors 1 and 2 have been cloned (Szebenyi et al., 1995). The vertebrate FGFRs contain the domains as described by Johnson and Williams, (1993). Modifications of FGFR isoforms are due to alternative splicing of the pre-mRNAs for each gene. In a schematic representation of human FGFR1, the extracellular region of the molecule has the following domains including a signal peptide region at its N-terminus, followed by three immunoglubulin-like (Ig-like) domains with an acid box between domain I and II. A membrane-proximal region precedes the transmembrane (TM) region. On the intracellular side, two tyrosine kinase domains that are separated by a kinase insert follow a juxtamembrane (JM) domain, and at the C-terminus is a C-tail domain. The third Ig-loop of FGF receptor 2 is involved in the chondrogenic process and can contain either the IIIa and IIIb (kgfr) or IIIa and IIIc (bek) exonic sequences (Johnson and Williams, 1993).

Using chick limb micromass culture, Szebenyi et al. (1995) have looked at changes in the expression of the FGFRs in differentiated cartilage and have found transcripts for fgfr1 in undifferentiated proliferating mesenchyme, fgfr2 in precartilage condensations, and fgfr3 in differentiating cartilage nodules suggesting spatiotemporal regulation in limb development. Binding of the FGFs to their receptors plays an important role in limb development through the regulation of cell survival, proliferation, and precartilage cell differentiation (Fallon et al., 1994; MacCabe et al., 1991; Niswander et al., 1993; Schofield and Wolpert, 1990; Szebenyi et al., 1995; Watanabe and Ide, 1993).

The messenger RNA splice variants IIIb (kgfr) and IIIc (bek) from fgfr1 and fgfr2, as well as fgfr3 were detected in nuclease protection assays on chicken limbs (Szebenyi et al., 1995). In addition, micromass cultures of stage 23-24 wing buds and in situ hybridization of stage 18, 23, 26, and 36 wings showed a spatial distribution of messenger RNA for fgfr1, 2, and 3. Furthermore, the probes for fgfr1 and 2 contained sequences for both the kgfr and bek splice variants and did not allow for the in vivo or in vitro detection of either of these isoforms. This is critical since there is a cell type specific role for the fibroblast growth factor receptor 2 isoforms, (FGFR2) kgfr (exon 8-IIIb) and bek (exon 9-IIIc), in precartilage differentiation. In addition, fibroblast growth factors (FGFs) influence cell function in a tissue-specific or developmental manner that can lead to defects such as craniosynostosis and syndactyly (Del Gatto, 1996; Mayeda and Krainer, 1992; Oldridge et al., 1999). This differential splicing of the pre-mRNAs produced by a single gene allows for the production of splice variants and results in forms that respond to the different growth factor isoforms in a highly specific manner. Cells that will differentiate into epithelia splice only the kgfr exon, while mesenchymal cells, including fibroblasts, as well as other cell types including endothelial cells, splice the 5' distal bek exon (Del Gatto, 1996; Fallon et al., 1994; Johnson and Williams, 1993; Rubin et al., 1989; Szebenyi et al., 1995).

Mutations in the various receptors cause various skeletal defects (Oldridge et al., 1999). Pfeiffer syndrome, a mutation in the fgfr1 gene, presents with craniosynostosis as well as limb defects; Crouzon syndrome, a result of a mutation in the fgfr2 gene, presents with limb abnormalities; and type II achondroplasia or dwarfism, is caused by a mutation in the fgfr3 gene (Szebenyi et al., 1995). Apert syndrome or acrocephalosyndactyly type 1, presents with head, hand, and foot abnormalities (Anderson et al., 1999). Oldridge et al. (1999) looked at mutations in the fgfr2 gene of 260 unrelated Apert syndrome patients and found that 258 individuals have a missense mutation in exon 7 which lies between the 2nd and 3rd Ig-like loop domains. The remaining two individuals had an ~360 bp insertion of an Alu-element either 5' to exon 9 or within exon 9, which arose as de novo mutations in the paternal chromosome (Oldridge et al., 1999). Exon 9 corresponds to the 3rd Ig-like loop domain and contains the bek (IIIc) sequence (Oldridge et al., 1999). In early studies involving the role of the fgfr2 splice variants IIIb (exon 8) and IIIc (exon 9), Rubin et al. (1989) found that keratinocytes expressed the FGFR2 IIIb isoform and were stimulated by KGF. In addition, fibroblasts and endothelial cells expressed the FGFR2 IIIc isoform, and responded to FGF2 (bFGF) (Johnson and Williams, 1993; Rubin et al., 1989). In an RNA analysis of fibroblasts obtained from two Apert and two Pfeiffer syndrome patients having mutations in exon 9, severity of limb abnormalities directly corresponded to ectopic expression of the of the IIIc-kgfr form of the FGFR2. These data provided evidence of the role of signal transduction pathways through the KGFR form of the receptor in relation to syndactyly in Apert syndrome (Oldridge et al., 1999; Park et al., 1995; Wilkie et al., 1995).

FIG. 4 illustrates FGFR2 with positional mutations, polymorphic nucleotides, and primers using in the Oldridge study. Top shows leader sequence (L), acid box (A), three Ig-like domains (IgI, IgIII, and IgIII), a transmembrane region (TM), and a split tyrosine-kinase domain (TK1 and TK2). Exons 8 and 9 encode for the alternative splice variants of the second a half of the IgIII domain, which is depicted by the IgIIIb (kgfr isoform) and IgIIIc (bek isoform) respectively. Positional mutations of two Apert syndrome patients (1 and 2) with Alu insertions, as well as two patients with Pfeiffer syndrome (3 and 4) with nucleotide substitutions are also shown. After Oldridge et al., (1999)

Alternative Splicing

An embodiment of the present invention describes a method and reagents that influence alternative splicing in living cells. Alternative splicing is a mechanism by which a single gene may eventually give rise to several different proteins. Alternative splicing is accomplished by the concerted action of a variety of different proteins, termed "alternative splicing regulatory proteins," that associate with the pre-mRNA in the cell nucleus, and cause distinct alternative exons to be included in the mature mRNA. These alternative forms of the gene's transcript give rise to distinct isoforms of the specified protein. The virulence of the HIV virus associated with AIDS depends on particular alternative splice choices, and several cancers, rheumatoid and osteoarthritis, and other inflammatory diseases, exhibit aberrant splice choices when compared to corresponding non-diseased tissues.

An embodiment of the present invention describes a novel means for influencing splice choice in living cells using polynucleotide-based reagents that compete for binding sites in alternative splicing regulatory proteins, and novel methods for using these reagents as therapeutics.

An embodiment of the present invention contains the following novel aspects, which will be taken up in order:

1. A novel method for influencing splice choice in living cells using polynucleotide-based reagents that compete for binding sites in alternative splicing regulatory proteins.

Sequences in pre-mRNA molecules that bind to alternative splicing regulatory proteins can be found in introns or exons, and are known by the terms intronic splicing silencers or enhancers, and exonic splicing silencers or enhancers (ISS, ISE, ESS, ESE). No published paper in the Medline database reports the introduction into living cells of polynucleotide-based competitors for ISS, ISE, ESS, or ESE binding sites in alternative splicing factors. Burd, C. G., and Dreyfuss, G. (1994) identified a 20-mer RNA sequence that binds the alternative splicing factor hnRNP A1, but this was work done with isolated protein and nucleic acid components, not within living cells. Blanchette, M., and Chabot, B. (1999) and Breathnach and co-workers (Del Gatto, F., and Breathnach, R., 1995; Del Gatto, F., Gesnel, M. C., and Breathnach, R., 1996; Del Gatto, F., Plet, A I, Gesnel, M. C., Fort, C., and Breathnach, R., 1997; Del Gatto-Konczak, F., Olive, M., Gesne, M. C., and Breathnach, R., 1999; have investigated the effects of various ISS, ISE, ESS, ESE-related sequences in splice choice in cell-free extracts, not within living cells.

2. Novel methods for using the reagents described above as therapeutics.

Although it has been recognized for some time that the life cycle of the AIDS virus HIV involves alternative splicing (Amendt, B. A., Si, Z. H., and Stoltzfus, C. M., 1995; Si, Z., Amendt, B. A., and Stoltzfus, C. M., 1997; Si, Z. H., Rauch, D., and Stoltzfus, C. M., 1998; Del Gatto-Konczak, F., Olive, M., Gesnel, M. C., and Breathnach, R., 1999; none of these, nor any other, studies propose treating the disease with competitors of ISS, ISE, ESS, or ESEs.

However, it is likely that if agents that competed with alternative splicing regulatory proteins such as hnRNP A1 for the HIV tat protein ESS were introduced into HIV infected cells, as shown in the Dissertation of one of the inventors "Avian hnRNP A1, an mRNA Shuttle Protein-Exon Splicing Silencer: Developmental Regulation and Role in Chondrogenesis" (Department of Cell Biology and Anatomy, New York Nedical College), which is herein incorporated by reference in its entirety, indicates that the method is feasible and effective, and that the the viral infection would be attenuated (Purcell, D. F., and Martin, M. A., 1993). Indeed, splicing of HIV-1 pre-mRNA must be inefficient to provide a pool of unspliced messages which encode viral proteins and serve as genomes for new virions (Caputi, M., Mayeda, A., Krainer, A. R., and Zahler, A. M., 1999), and virus production is arrested in a natural HIV variant that has an aberrant ESS (Wentz, M. P., Moore, B. E., Cloyd, M. W., Berget, S. M., and Donehower, L. A., 1997).

With regard to cancer, it has been found that certain tumors, such as mammary carcinomas (Stickeler, E., Kittrell, F., Medina, D., and Berget, S. M., 1999) and colon adenocarcinomas (Ghigna, C., Moroni, M., Porta, C., Riva, S., and Biamonti, G., 1998) contain levels of hnRNP A1 and other alternative splicing regulatory proteins that are altered relative to related normal tissues. Moreover, this abnormality is reflected in aberrant splicing patterns of certain alternatively spliced gene products, such as the cell adhesive protein CD44, although the specific role of splice variants of CD44 in tumorigenicity and metastasis is unresolved (Sneath, R. J., and Mangham, D. C., 1998).

The neoplastic state is characterized by numerous other gene products that show aberrant alternative splicing patterns. These include the extracellular matrix protein fibronectin (Midulla, M. Verma, R., Pitnatelli, M., Ritter, M. A., Courtenay-Luck, N. S., and George, A. J., 2000), the proteolytic enzyme cathepsin B (Keppler, D., and Sloane, B. F., 1996), the breast cancer susceptibility gene BRCA2 (Bieche, I., and Lidereau, R., 1999), and the apoptosis-associated gene products Bcl-x (Xerri, L., Hassoun, J., Devilard, E., Birnbaum, D., and Birg, F., 1998), Bax (Oltvai, Z. N., Milliman, C. L., and Korsmeyer, S. J., 1993), and caspase 2 (Ich-1) (Jiang, Z. H., and Wu, J. Y., 1999). The apparent causal relationship of some of these aberrant splicing patterns to the neoplastic state, coupled with the emerging evidence that tumors express abnormal levels of alternative splicing regulatory proteins, suggest that treatment with agents that specifically inhibit these regulatory proteins, such as those methods and reagents disclosed and claimed herein, represent a promising approach to cancer therapy.

Inflammatory diseases such as rheumatoid and osteoarthritis also involve protein (e.g., CD44) that exhibit abnormal alternative splicing patterns (Croft, D. R., Dall, P., Davies, D., Jackson, D. G., McIntyre, P., and Kamer, L. M., 1997; Boyle D. L., Shi, Y., Gat, S., and Firestein, G. S., 2000), and it is reasonable to hypothesize that the resulting aberrant proteins, among which are secreted and cell surface molecules, contribute to the immune-mediated manifestations of these diseases. Again, these data suggest that treatment with agents that specifically target alternative splicing factors represent a promising therapeutic approach.

Several publications have suggested using an antisense strategy to alter splicing patterns as therapeutics for cancer and ceratin other diseases (but not AIDS) (Sierakowska, H., Gorman, L., Kang, S. H., and Kole, R. (2000); Mercatante, D., and Kole, R., 2000). The invention described herein is not an antisense strategy, and has many advantages over such a strategy.

Current treatment of AIDS uses multiple reagents (AXT, protease inhibitors) directed against different biological functions of HIV. The method and reagents according to an embodiment of the present invention are directed against a distinct cell-virus interactive function, alternative splicing, and should add productively to the spectrum of agents available for treatment of this disease. Current treatment for cancer involves the use of agents that are frequently highly toxic and nonspecific. The method and reagents according to an embodiment of the present invention will constitute therapeutics with high specificity for a biological function, alternative splicing, that is aberrant in many cancers.

SUMMARY OF THE INVENTION

In response to the foregoing challenge, Applicants have developed an innovative, economical method of modifying the activity of nucleotide binding proteins within cells comprising introducing into cells polynucleotide sequences capable of binding to nucleotide binding proteins, binding within cells the polynucleotide sequences to the nucleotide binding proteins, and modifying within cells the activity of the nucleotide binding proteins with the binding.

The polynucleotide sequences may be introduced into the cells by electroporation, by applying the polynucleotide sequences to the surface of the cells, by packaging the polynucleotide sequences in liposomes, and by applying the polynucleotide sequences to the surface of the cells along with a detergent.

The cells may be human cells, tissue culture cells, non-human cells, non-human mammalian cells, avian cells, and non-human tissue culture cells.

The polynucleotide sequences may comprise RNA, isolated and purified RNA molecules, synthetic RNA molecules, and synthetic RNA analogs (chemical compositions similar to RNA), DNA, isolated and purified DNA molecules, synthetic DNA molecules, and synthetic DNA analogs (chemical compositions similar to DNA). The polynucleotide sequences may be single-stranded or double-stranded.

The step of modifying within cells the activity of the nucleotide binding proteins may comprise regulating the activity of the nucleotide binding proteins, reducing the activity of the nucleotide binding proteins, and/or blocking the activity of the nucleotide binding proteins. The binding of the polynucleotide sequences may be reversible or irreversible.

The method may further comprise the step of causing an effect within cells in the processing of RNA by modifying the activity of the nucleotide binding proteins.

The method may further comprise the step of determining the effect in the processing of RNA by the resulting phenotypic characteristics of the cells, and/or by Northern blot analysis of cell extracts.

Another embodiment of the present invention is a method of modifying the activity of RNA binding proteins within cells comprising introducing into cells polynucleotide sequences capable of binding to RNA binding proteins, binding within cells the polynucleotide sequences to the RNA binding proteins, and modifying within cells the activity of the RNA binding proteins with said binding. The method may further comprise the step of causing an effect within cells in the processing of RNA by modifying the activity of the RNA binding proteins.

Another embodiment of the present invention is a method of modifying the activity of RNA alternative splicing regulatory proteins within cells comprising: a) introducing into cells polynucleotide sequences capable of binding to RNA alternative splicing regulatory proteins; b) binding within cells the polynucleotide sequences to the RNA alternative splicing regulatory proteins; and c) modifying within cells the activity of the RNA alternative splicing regulatory proteins with said binding.

Another embodiment of the present invention is a method of modifying the activity of hnRNP proteins within cells comprising: a) introducing into cells polynucleotide sequences capable of binding to hnRNP proteins; b) binding within cells the polynucleotide sequences to the hnRNP proteins; and c) modifying within cells the activity of the hnRNP proteins with the binding.

Another embodiment of the present invention is method of modifying the activity of hnRNP A1 proteins within cells comprising: a) introducing into cells polynucleotide sequences capable of binding to hnRNP A1 proteins; b) binding within cells the polynucleotide sequences to the hnRNP A1 proteins; and c) modifying within cells the activity of the hnRNP A1 proteins with the binding.

Another embodiment of the present invention is a method of modifying the activity of nucleotide binding proteins within cells comprising: a) introducing into cells polynucleotide sequences complementary to binding sites of nucleotide binding proteins; b) binding within cells the polynucleotide sequences to the nucleotide binding proteins; and c) modifying within cells the activity of the nucleotide binding proteins with the binding. The nucleotide Binding proteins may be RNA binding proteins, RNA alternative splicing regulatory proteins, hnRNP proteins, and/or hnRNP A1 proteins.

An alternative embodiment of the present invention is a method of modifying the activity of nucleotide binding proteins within cells comprising: a) introducing into cells polynucleotide sequences that bind to nucleotide binding proteins; b) binding within cells the polynucleotide sequences to the nucleotide binding proteins; and c) modifying within cells the activity of the nucleotide binding proteins with the binding.

An alternative embodiment of the present invention is a method of influencing splice choice in RNA within cells comprising: a) introducing into cells polynucleotide sequences that bind to nucleotide binding proteins; b) binding within cells the polynucleotide sequences to the nucleotide binding proteins; and c) modifying within cells the activity of the nucleotide binding proteins with the binding.

An alternative embodiment of the present invention is a composition comprising a non-naturally occuring polynucleotide sequence that binds within cells to an hnRNP A1 protein of Seq. ID No. 2 and modifies the activity of the hnRNP A1 protein. The non-naturally occuring polynucleotide sequence may be a synthetic polynucleotide sequence, and/or a polynucleotide sequence analog. The non-naturally occuring polynucleotide sequence may bind to an hnRNP A1 protein of Seq. ID No. 2 under physiological conditions and modify the activity of the hnRNP A1 protein. The non-naturally occuring polynucleotide sequence may influence RNA splice choice within cells by modifying the activity of the nucleotide binding proteins.

An alternative embodiment of the present invention is a composition comprising a non-naturally occuring polynucleotide sequence bound to an hnRNP A1 protein.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

FIG. 1a is a listing of the full length cDNA sequence of chicken hnRNP A1 designated as SEQ ID NO:1. Uppercase letters indicate the open reading frame designated as SEQ ID NO:4.

FIG. 1b is a listing of the translation product of SEQ ID NO:4, designated as SEQ ID NO:2 aligned with the amino acid sequence of human hnRNP A1 designated as SEQ ID NO:3.

DETAILED DESCRIPTION OF THE PREFERRED EMBODIMENTS

Figure 2:
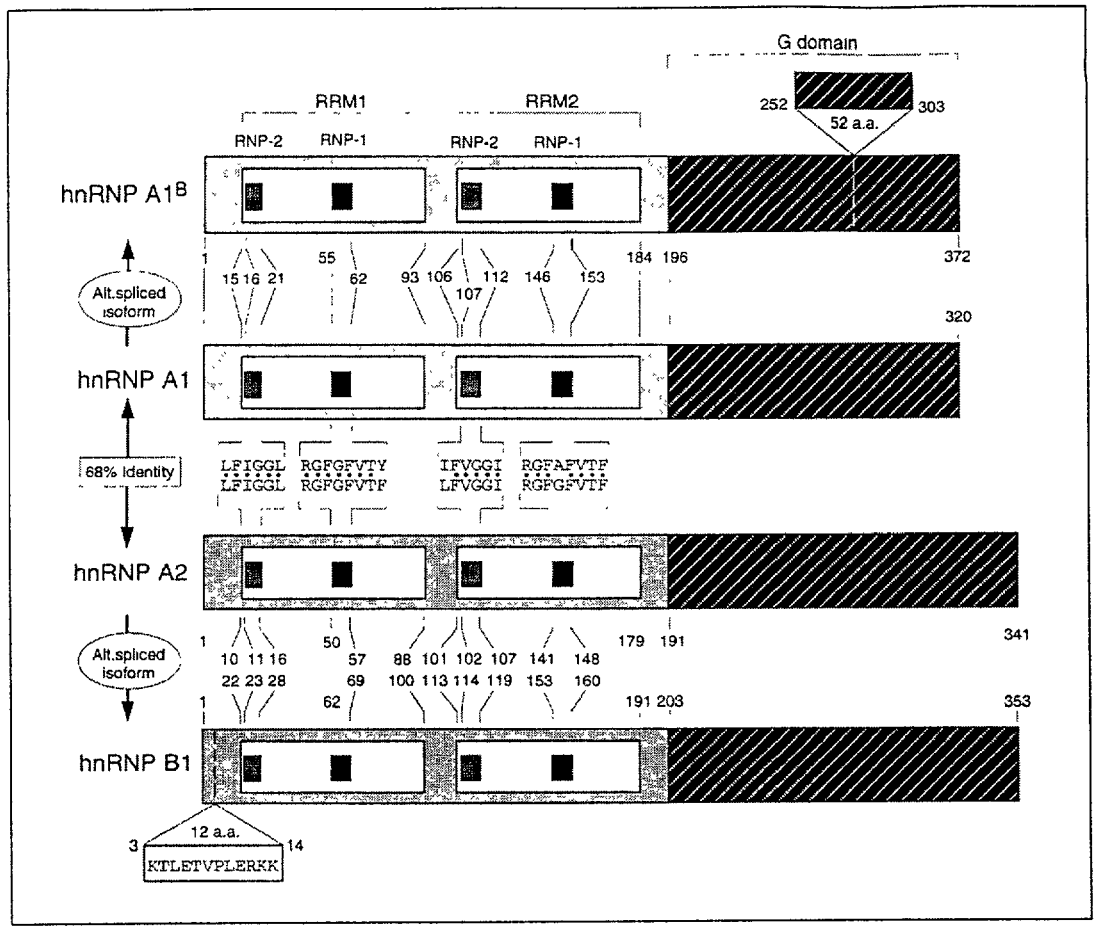
FIG. 2 is a schematic representation of the structure of the human core hnRNP proteins A1, A1B, A2, and B1.

The present invention comprises a method of modifying the activity of nucleotide binding proteins within cells. A preferred embodiment of the method of the present invention comprises introducing into cells polynucleotide sequences that bind to nucleotide binding proteins, modifying within cells the activity of the nucleotide binding protein by binding the polynucleotides to the nucleotide binding proteins, causing an effect within the cells in the processing of RNA by modifying the activity of the nucleotide binding proteins, and determining the effect in the processing of RNA resulting from the modification of the activity of the nucleotide binding proteins. The step of introducing into cells polynucleotide sequences may further comprise introducing the polynucleotide by electroporation. The step of introducing into cells polynucleotide sequences may further comprise introducing the polynucleotide sequences by applying the polynucleotide sequence to the surface of the cells. The step of introducing into cells polynucleotide sequences may further comprise introducing the polynucleotide sequences by applying the polynucleotide sequences to the surface of the cells packaged in liposomes. The step of introducing into cells polynucleotide sequences may further comprise introducing the polynucleotide sequences by applying the polynucleotide sequence to the surface of the cells along with a detergent.

The step of modifying within cells the activity of the nucleotide binding proteins may further comprise regulating the activity of the nucleotide binding protein. The step of modifying within cells the activity of the nucleotide binding proteins may further comprise reducing the activity of the nucleotide binding proteins. The step of modifying within cells the activity of the nucleotide binding proteins may further comprise blocking the activity of the nucleotide binding proteins. The step of modifying within cells the activity of the nucleotide binding proteins may further comprise binding the polynucleotides either reversibly, or irreversibly.

As embodied herein, the step of determining the effect in the processing of RNA may further comprise determining the effect by phenotypic characteristics of the cells. The step of determining the effect in the processing of RNA may further comprise determining the effect by Northern blot analysis of cell extracts.

As embodied herein, the cells may further comprise tissue culture cells, and non-human tissue culture cells. The cells may also further comprise non-human cells, non-human mammalian cells, and avian cells.

As embodied herein, the polynucleotide sequences may further comprise isolated and purified RNA molecules, synthetic RNA molecules, and synthetic RNA analogs. The polynucleotide sequences may be single stranded.

An alternative preferred embodiment of the present invention is a method of modifying the activity of RNA binding proteins within cells comprising introducing into cells polynucleotide sequences that bind to RNA binding proteins, modifying within cells the activity of the RNA binding proteins by binding the polynucleotides to the RNA binding proteins, causing an effect within cells in the processing of RNA by modifying the activity of the RNA binding proteins, and determining the effect resulting from the modification of the activity of the RNA binding proteins. The step of introducing into cells polynucleotide sequences may further comprise introducing the polynucleotide by electroporation. The step of introducing into cells polynucleotide sequences may further comprise introducing the polynucleotide sequences by applying the polynucleotide sequence to the surface of the cells. The step of introducing into cells polynucleotide sequences may further comprise introducing the polynucleotide sequences by applying the polynucleotide sequences to the surface of the cells packaged in liposomes. The step of introducing into cells polynucleotide sequences may further comprise introducing the polynucleotide sequences by applying the polynucleotide sequence to the surface of the cells along with a detergent.

The step of modifying within cells the activity of the RNA binding proteins may further comprise regulating the activity of the RNA binding proteins. The step of modifying within cells the activity of the RNA binding proteins may further comprise reducing the activity of the RNA binding proteins. The step of modifying within cells the activity of the RNA binding proteins may further comprise blocking the activity of the RNA binding proteins. The step of modifying within cells the activity of the RNA binding proteins may further comprise binding the polynucleotides either reversibly, or irreversibly.

As embodied herein, the step of determining the effect in the processing of RNA may further comprise determining the effect by phenotypic characteristics of the cells. The step of determining the effect in the processing of RNA may further comprise determining the effect by Northern blot analysis of cell extracts.

As embodied herein, the cells may further comprise tissue culture cells, and non-human tissue culture cells. The cells may also further comprise non-human cells, non-human mammalian cells, and avian cells.

As embodied herein, the polynucleotide sequences may further comprise isolated and purified RNA molecules, synthetic RNA molecules, and synthetic RNA analogs. The polynucleotide sequences may be single stranded.

An alternative preferred embodiment of the present invention is a method of modifying the activity of RNA alternative splicing regulatory proteins within cells comprising introducing into cells polynucleotide sequences that bind to the RNA alternative splicing regulatory proteins, modifying within cells the activity of the RNA alternative splicing regulatory proteins by binding the polynucleotides to the RNA alternative splicing regulatory proteins, causing an effect within cells in the processing of RNA by modifying the activity of the RNA alternative splicing regulatory proteins, and determining the effect resulting from themodification of the activity of the RNA alternative splicing regulatory proteins. The step of introducing into cells polynucleotide sequences may further comprise introducing the polynucleotide by electroporation. The step of introducing into cells polynucleotide sequences may further comprise introducing the polynucleotide sequences by applying the polynucleotide sequence to the surface of the cells. The step of introducing into cells polynucleotide sequences may further comprise introducing the polynucleotide sequences by applying the polynucleotide sequences to the surface of the cells packaged in liposomes. The step of introducing into cells polynucleotide sequences may further comprise introducing the polynucleotide sequences by applying the polynucleotide sequence to the surface of the cells along with a detergent.

The step of modifying within cells the activity of RNA alternative splicing regulatory proteins may further comprise regulating the activity of RNA alternative splicing regulatory proteins. The step of modifying within cells the activity of RNA alternative splicing regulatory proteins may further comprise reducing the activity of RNA alternative splicing regulatory proteins. The step of modifying within cells the activity of the RNA alternative splicing regulatory proteins may further comprise blocking the activity of the RNA alternative splicing regulatory proteins. The step of modifying within cells the activity of the RNA alternative splicing regulatory proteins may further comprise binding the polynucleotides either reversibly, or irreversibly.

As embodied herein, the step of determining the effect in the processing of RNA may further comprise determining the effect by phenotypic characteristics of the cells. The step of determining the effect in the processing of RNA may further comprise determining the effect by Northern blot analysis of cell extracts.

As embodied herein, the cells may further comprise tissue culture cells, and non-human tissue culture cells. The cells may also further comprise non-human cells, non-human mammalian cells, and avian cells.

As embodied herein, the polynucleotide sequences may further comprise isolated and purified RNA molecules, synthetic RNA molecules, and synthetic RNA analogs. The polynucleotide sequences may be single stranded.

An alternative preferred embodiment of the present invention is a method of modifying the activity of hnRNP A1 proteins within cells comprising introducing into cells polynucleotide sequences that bind to hnRNP A1 proteins, modifying within cells the activity of hnRNP A1 proteins by binding the polynucleotides to the hnRNP A1 proteins, causing an effect within cells in the processing of RNA by modifying the activity of the hnRNP A1 proteins, and determining the effect resulting from the modification of the activity of the hnRNP A1 proteins. The step of introducing into cells polynucleotide sequences may further comprise introducing the polynucleotide by electroporation. The step of introducing into cells polynucleotide sequences may further comprise introducing the polynucleotide sequences by applying the polynucleotide sequence to the surface of the cells. The step of introducing into cells polynucleotide sequences may further comprise introducing the polynucleotide sequences by applying the polynucleotide sequences to the surface of the cells packaged in liposomes. The step of introducing into cells polynucleotide sequences may further comprise introducing the polynucleotide sequences by applying the polynucleotide sequence to the surface of the cells along with a detergent.

The step of modifying within cells the activity of the hnRNP A1 proteins may further comprise regulating the activity of the hnRNP A1 proteins. The step of modifying within cells the activity of the hnRNP A1 proteins may further comprise reducing the activity of the hnRNP A1 proteins. The step of modifying within cells the activity of the hnRNP A1 proteins may further comprise blocking the activity of the hnRNP A1 proteins. The step of modifying within cells the activity of the hnRNP A1 proteins may further comprise binding the polynucleotides either reversibly, or irreversibly.

As embodied herein, the step of determining the effect in the processing of RNA may further comprise determining the effect by phenotypic characteristics of the cells. The step of determining the effect in the processing of RNA may further comprise determining the effect by Northern blot analysis of cell extracts.

As embodied herein, the cells may further comprise tissue culture cells, and non-human tissue culture cells. The cells may also further comprise non-human cells, non-human mammalian cells, and avian cells.

As embodied herein, the polynucleotide sequences may further comprise isolated and purified RNA molecules, synthetic RNA molecules, and synthetic RNA analogs. The polynucleotide sequences may be single stranded.

An alternative preferred embodiment of the present invention is a method of influencing splice choice in RNA within cells comprising introducing into cells polynucleotide sequences that bind to RNA splicing regulatory proteins, modifying within cells the activity of the RNA splicing regulatory proteins, modifying within cells the activity of the RNA splicing regulatory proteins by binding the polynucleotides to the RNA splicing regulatory proteins, causing an effect within cells in the processing of RNA by modifying the activity of the RNA splicing regulatory proteins, and determining the effect in the processing of RNA resulting from the modification of the activity of the RNA splicing regulatory proteins. The step of introducing into cells polynucleotide sequences may further comprise introducing the polynucleotide by electroporation. The step of introducing into cells polynucleotide sequences may further comprise introducing the polynucleotide sequences by applying the polynucleotide sequence to the surface of the cells. The step of introducing into cells polynucleotide sequences may further comprise introducing the polynucleotide sequences by applying the polynucleotide sequences to the surface of the cells packaged in liposomes. The step of introducing into cells polynucleotide sequences may further comprise introducing the polynucleotide sequences by applying the polynucleotide sequence to the surface of the cells along with a detergent.

The step of modifying within cells the activity of the RNA splicing regulatory proteins may further comprise regulating the activity of the RNA splicing regulatory proteins. The step of modifying within cells the activity of the RNA splicing regulatory proteins may further comprise reducing the activity of the RNA splicing regulatory proteins. The step of modifying within cells the activity of the RNA splicing regulatory proteins may further comprise blocking the activity of the RNA splicing regulatory proteins. The step of modifying within cells the activity of the RNA splicing regulatory proteins may further comprise binding the polynucleotides either reversibly, or irreversibly.

As embodied herein, the step of determining the effect in the processing of RNA may further comprise determining the effect by phenotypic characteristics of the cells. The step of determining the effect in the processing of RNA may further comprise determining the effect by Northern blot analysis of cell extracts.

As embodied herein, the cells may further comprise tissue culture cells, and non-human tissue culture cells. The cells may also further comprise non-human cells, non-human mammalian cells, and avian cells.

As embodied herein, the polynucleotide sequences may further comprise isolated and purified RNA molecules, synthetic RNA molecules, and synthetic RNA analogs. The polynucleotide sequences may be single stranded.

EXAMPLE 1

Inhibition of hnRNP A1 Function

To test the hypothesis that hnRNP A1 is involved selecting the correct splice choice variant of FGFR2, exon competition assays were designed. The following competition studies were performed with the hypothesis that the ASF/SF2 and hnRNP A1 are antagonists and make splice choice selections in the third exon loop of the fgfr2 pre-mRNA (Caceres et al., 1998; Caceres et al., 1994; Mayeda and Krainer, 1992; Yang et al., 1994). ASF/SF2 preferentially selects the proximal splice choice IIIb exon, while hnRNP A1 selects the distal splice variant IIIc by binding to the ESS sequence in the IIIb exon (Del Gatto-Konczak et al., 1999). Splice choice selection is based on the relative concentration of the two splicing factors so that high ASF/SF2 concentration yields the IIIb mRNA splice variant and production of the FGFR2IIIb isoform of the receptor and should result in a fused cartilage phenotype rather than discrete nodules.

The distal tips of stage 25 chicken leg buds were electroporated with the 138 base sense transcript from the chicken fgfr2IIIb mRNA containing the ESS corresponding to exon 8. As a control, leg buds were also electroporated with the 141 base sense transcript from the chicken fgfr2IIIc mRNA corresponding to exon 9. Transfected cultures were grown in serum-free medium and stained as previously described. Cultures transfected with exon 9 displayed discrete nodules as expected (Downie and Newman, 1994). When cultures were transfected with exon 8 containing the ESS a continuous mass of cartilage formed with extensive cartilage formation in the central region again with few residual nodules at the periphery (FIG. 5a). When cultures were transfected with exon 8 transcript, a continuous mass of cartilage formed in the central region, again with few residual nodules at the periphery (FIG. 5b). This was most likely due to the interaction of the endogenous splice choice factor, in this case, hnRNP A1, with the exogenous exon 8 transcript containing the ESS sequence. Although hnRNP A1 is also involved in making splice choices of its own pre-mRNA, this process is accomplished by binding at intronic sites rather than exonic sites, as with FGFR2. The transfection of cultures with exogenous exon 8 would therefore not be expected to interfere with the correct processing of hnRNP A1 pre-mRNA.

By the hypothesis presented above, the lack of availability of hnRNP A1 should lead to expression of the incorrect kgfr (IIIb) splice variant rather than the correct bek (IIIc) FGFR2 isoform. As noted above, this missplicing also occurs in certain severe Apert syndrome cases as a result of Alu-element insertions in the FGFR2 gene (Oldridge et al., 1999).

EXAMPLE 2

The ribonucleoprotein hnRNP A1 plays a role in both RNA splice site selection and nucleus-to-cytoplasm transport of mRNA. In its capacity as a splicing factor, this protein modulates 5' splice site selection in a group of gene products containing a well-characterized RNA sequence determinant, the exonic splicing silencer (ESS). The HIV type 1 tat protein, the FGFR2 (Caputi et al., 1999; Del Gatto-Konczak et al., 1999; Mayeda et al., 1994), and hnRNP A1 are among the pre-mRNAs that undergo differential splicing (Chabot et al., 1997). In its role in nucleus-to-cytoplasm transport, hnRNP A1 acts as a "shuttle" protein, and is characterized by a novel amino acid motif found at its C-terminus termed M9, which contains both nuclear localization and nuclear export activities (Nakielny and Dreyfuss, 1997a; Nakielny et al., 1999).

hnRNP A1 transcripts and protein are localized in whole and sectioned 4½-12 day embryos, as well in limb bud micromass cultures. In whole and sectioned tissue, expression has been detected in the skin, heart, gizzard, liver, lung, vertebral bodies, neural tissue, intestine, kidney tubules, and developing limb cartilage. In the developing cartilage of the vertebrae and limbs hnRNP A1 protein is initially present in precartilage cell condensations and persists in early chondrocytes. Earlier studies have looked at the distribution of hnRNP A1 in various differentiated cell types as well as in developing germ line cells of postnatal mice (Faura et al., 1995; Kamma et al., 1995). These studies demonstrated that hnRNP A1 was expressed at higher levels in earlier stages of spermatocyte development (Kamma et al., 1995). The studies described in this thesis represent the first systematic analysis of hnRNP A1's expression during embryogenesis.

The functional significance of the stage-dependent hnRNP A1 expression patterns seen during development is dependent in part on the role of this protein in alternative splicing. One developmentally important gene whose transcript is alternatively spliced with the participation of hnRNP A1 is fibroblast growth factor receptor 2 (FGFR2) where it is involved in the choice of exon 9 rather than exon 8 (Del Gatto-Konczak et al., 1999). Because (i) FGFR2 has a known pattern of spatiotemporal expression during appendicular chondrogenesis (Peters et al., 1992; Lizarraga et al., 1999; Szebenyi and Fallon, 1999), (ii) incorrect exon 8/exon 9 choice in FGFR2 in humans has known morphological consequences to the limb skeleton (Oldridge et al., 1999), and (iii) the studies described herein show hnRNP A1 to have a distribution in the developing limb coincident with that previously found for FGFR2, the remainder of the work described was directed towards testing whether interference with hnRNP A1 synthesis or function had the effects predicted on the basis of our current understanding of FGFR2 function in limb skeletal patterning.

The fibroblast growth factors (FGFs), of which 19 structural vertebrate polypeptide homologs have been identified (Ornitz, 2000), are major modulators of embryonic development. Their roles include the formation of the primary body and neural axes, limbs and other structures including the heart, liver, muscle, head and face, teeth, lung, pancreas, skin, salivary glands, as well as the trophoectoderm and the inner cell mass of pregastrulating mammalian embryos (Arman et al., 1999; Burke et al., 1998; Chan and Thorogood, 1999; De Moerlooze et al., 2000; Eckenstein, 1994; Hajihosseini and Dickson, 1999; Jang et al., 1997; Jung et al., 1999; Kettunen et al., 1998; Olwin et al., 1994; Patstone et al., 1993; Szebenyi and Fallon, 1999; Wilke et al., 1997; Zhu et al., 1999). By affecting gene expression, FGFs coordinate cellular functions including survival, replication, differentiation, adhesion and motility (Szebenyi and Fallon, 1999).

FGFs bind to cell surface receptors including (i) FGF receptor tyrosine kinases 1-4, (ii) a cytosine rich FGF receptor, and (iii) heparan sulfate proteoglycans (HSPGs) (Jang et al., 1997; Lin et al., 1999; Olwin et al., 1994; Ornitz, 2000). Signaling through FGFs requires both the high affinity FGFRs and low affinity HSPGs to form an active complex (Aviezer et al., 1999; Eckenstein, 1994; Lin et al., 1999; Olwin et al., 1994; Ornitz, 2000). In humans, mutations in FGFR1, -2, and -3 lead to five distinct craniosynostosis syndromes including Apert syndrome which arises from mutations in FGFR2 (Chan and Thorogood, 1999; Oldridge et al., 1997; Oldridge et al., 1995; Oldridge et al., 1999). Additional abnormalities are seen in the limbs, skin, teeth, and CNS of these individuals (Chan and Thorogood, 1999).

Differential splicing of FGFR2 at the third Ig-like loop produces the FGFR2IIIb and IIIc splice variants which are active in epithelial-mesenchyme differentiation (Arman et al., 1998; Orr-Urtreger et al., 1993). Earlier studies have shown that FGFR2IIIb is preferentially expressed in epithelial tissues and that FGFR2IIIc is expressed in the mesenchyme (Orr-Urtreger et al., 1993).

Proper patterning of the vertebrate limb relies on expression of hnRNP A1 and, as a consequence, the appropriate splice form of FGFR2. Previous work done by S. Downie (Ph.D. thesis, New York Medical College) showed that micromass leg cultures in the absence of ectoderm and in the presence of serum produced a continuous sheet of cartilage. In contrast, cells cultured in the presence of ectoderm produced individual nodules with regions of perinodular inhibition. Leg micromass cultures that were devoid of ectoderm but with the exogenous addition of the growth factor FGF2 formed discrete nodules with very large regions of inhibition. These findings suggest that limb skeletal pattern depends, in part, on an activator-inhibitor interaction (Newman et al., 1981a; Newman and Tomasek, 1996).

When limb bud precartilage mesenchymal cells are plated as high density micromass cultures, cells begin to condense and by day 6 after plating, will form cartilage nodules, which stain with alcian blue.

Based on previous data the following model is suggested for the phenomenon described in micromass cultures:
1. Limb bud mesenchymal cells anchor and produce the diffusible molecule TGFβ (Leonard et al., 1991; Miura and Shiota, 2000).
2. TGFβ auto-stimulates its own production (Van Obberghen-Schilling et al., 1988).
3. TGFβ also stimulates the production of hnRNP A1
4. hnRNP A1 determines the splice choice from the IIIb (kgfr) form to the IIIc(bek) form in FGFR2 pre-mRNA (Del Gatto-Konczak et al., 1999).
5. FGFR2 IIIc isoform is stimulated by FGFs and mediates the production of an unknown "inhibitor" which then downregulates TGFβ expression, allowing for the formation of spaces between the cartilage nodules.

When limb bud micromass cultures were treated with exogenous TGFβ they formed precocious cartilage nodules by 72 h. immunofluorescent detection of hnRNP A1 in these cultures shows that protein expression is within the condensing region. Confocal microscopy of normal 72 h cultures shows that all cells within the condensations are expressing high levels of the hnRNP A1 protein.

When leg limb bud tips were electroporated with hnRNP A1 antisense transcripts perinodular regions of inhibition were no longer detected and a continuous sheet of cartilage was seen. Western blot analysis of electroporated cultures confirmed that there was a decrease in the amount of hnRNP A1 protein detected in antisense treated cultures at 48 h. Furthermore, when antisense RNA directed against hnRNP A1 was introduced into a developing wing bud in ovo, a large mass of ectopic cartilage formed. These results indicate that lack of hnRNP A1 during the period of limb pattern formation lead to a lack of normal inhibition around developing cartilage elements, consistent with its role in the model described above.

Figure 5:
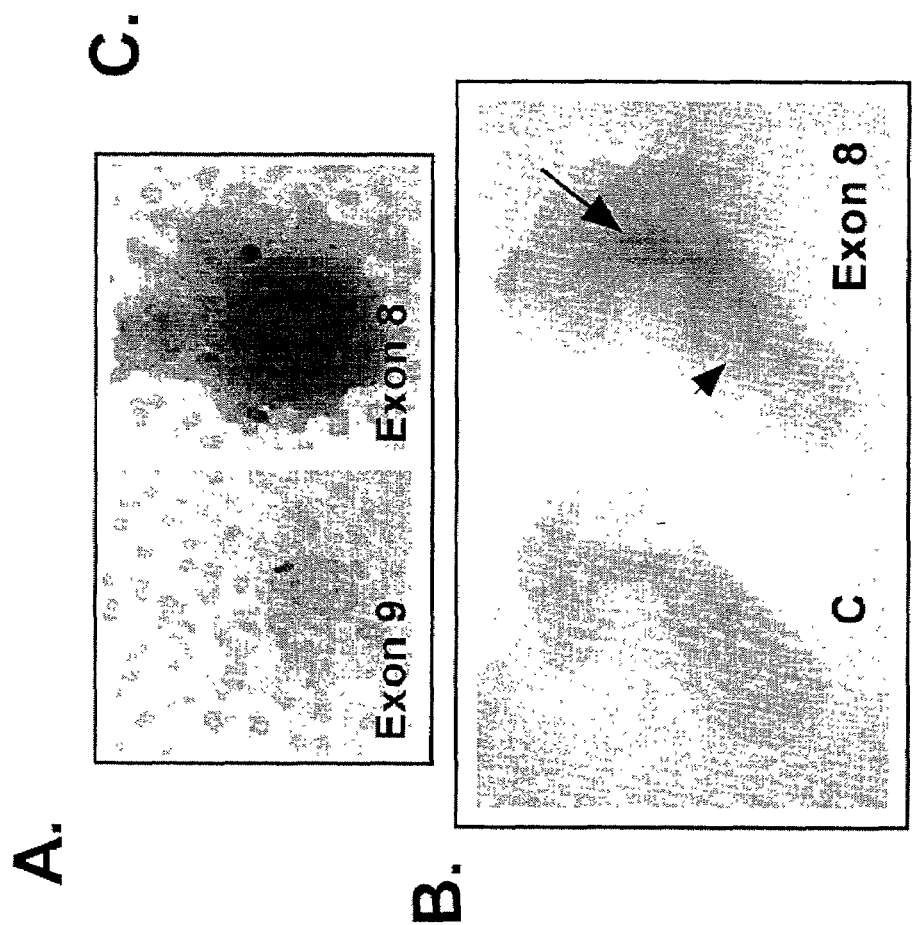
FIG. 5a is a photomicrograph of chicken leg bud mesenchymal cells transfected with FGFR2 exon 9 sense strand RNA and exon 8 sense strand RNA.
FIG. 5b is an x-ray of a developing chicken leg bud transfected with FGFR2 exon 8.
FIG. 5c is a Northern blot using poly A RNA from leg bud mesenchyme transfected with FGFR2 exon 8 or exon 9 sense strand RNA.

When limb bud tips were electroporated with FGFR2 exon 8, which contains the ESS consensus sequence for hnRNP A1 binding, the cartilage pattern was similar to that of cultures that were treated with hnRNP A1 antisense RNA. The model outlined above would predict that excess ESS sequence would interfere with the normal binding of hnRNP A1 to its target sequence in FGFR2. Since hnRNP A1 and SF2/ASF are antagonists for exon splicing the loss hnRNP A1 function will lead to the incorrect splice choice and the FGFR2IIIb instead of FGFR2IIIc. As predicted, transfection of exon 8 (but not exon 9) reduced the production of perinodular inhibitory activity (FIG. 5). Preliminary Northern blot results indicate that transfecting cultures with exon 8 interferes with the splicing of FGFR2 mRNA. In vivo, individuals with Alu elements in exon IIIC (exon 9) splice only exon IIIb (exon 8) and present with syndactyly (Oldridge et al., 1999).

These results also bear on the possible role of hnRNP A1 at the other sites in which it has been found during embryogenesis. While this splicing factor undoubtedly has a variety of targets, other than its role in self-splicing its role in FGFR2 is best understood. Therefore the spatiotemporal coordination of the expression of FGF receptors and hnRNP A1 will be emphasized in the following discussion.

In embryonic mice, FGFR2IIIb and IIIc mRNA splice variants have been localized in various tissues including the developing lung bud were the IIIb isoform was localized in the bronchial epithelia and limb ectoderm. The IIIc isoform was localized in the mesenchyme of the lung and developing limb buds (Arman et al., 1999). De Moerlooze et al. (2000) found that null mice for the FGFR2IIIb isoform were viable until birth but displayed severe limb, lung, and anterior pituitary gland defects with tissues undergoing apoptosis. Abnormalities were also detected in the salivary glands, inner ear, teeth, skin, and skull.

Chan and Thorogood (2000) looked at mutations in FGFR1 and 2 in 6-8 week human embryos and found that FGFR1 and FGFR2IIIb and IIIc isoforms were expressed in the enamel epithelium and papilla mesenchyme of the tooth germ. In addition, both genes are expressed in the cortical layer of the brain. Hajihosseini and Dickson (1999) showed that embryonic day 15 cultured rat cortical cells initially express FGFR1, -2, and -3IIIc isoforms but within 16 hours post culturing they downregulated the FGFR2IIIc splice variant. Wilke et al. (1997) looked at the role of FGFs in skull, brain, and facial prominence in differential growth in chicken embryos and correlated these findings to FGFR mutations in humans.

Using in situ hybridization techniques, Kettunen et al. (1998) analyzed FGFR1 and 2 expression patterns in mouse teeth. They found that the FGFR1IIIc splice variant was expressed in both the dental epithelium and mesenchyme while FGFR2IIIc was restricted to the dental follicle mesenchyme They suggested that FGFs regulated differentiation and secretory functions in both odontoblasts and ameloblasts through the FGFR1IIIc signaling pathway, with additional signaling through the FGFR2IIIc isoform in the ameloblasts.

Walsh and Mason (2000) looked at the expression of FGFR1, -2, and -3 transcripts in early neural development in chicken embryos. Other studies showed that FGFs can induce neural tissue to form from unstimulated epiblast (Alvarez et al., 1998; Storey et al., 1998; Walshe and Mason, 2000). Studies investigating the role of FGF4 and 8 demonstrated that FGF4 regulates the specification of the midbrain (Shamim et al., 1999) while FGF8 regulates isthmus and midbrain proliferation and polarization (Crossley et al., 1996; Martinez et al., 1999; Sheikh and Mason, 1996). During neural induction all three FGFRs transcripts were localized with the FGFR1IIIc isoform predominantly detected in the neural plate and mesendodermal cells. Both FGFR2IIIb and IIIc were localized in the anterior primitive streak and in the neural plate region close to the head process while FGFR3IIIc was localized in the lateral ectoderm anterior to Henson's node. In situ hybridization of Hamburger-Hamilton stage 17 embryos showed that FGFR2 was expressed in the mesonephric ducts as well as throughout the ectoderm. Finally, FGFR2 transcripts were localized to the ectoderm and AER of the developing limb bud of stage 17 embryos.

Patstone et al. (1993) suggested that expression of FGFR1, -2, and -3 in various chicken embryonic tissues including the developing bones, skeletal-, cardiac-, and smooth muscle, as well as areas of the brain, may represent cell-type specific regulation and that the ligand-receptor interaction may likely be controlled by spatiotemporal constraints.

Zhu et al. (1999) examined the role of FGFs on proliferation and terminal differentiation of precardiac mesodermal cells and endodermal cells in the heart forming region of stage 6 chicken embryos. Jung et al. (1999) looked at the relationship of FGF1, -2, and -8 produced by cardiac mesoderm and the induction of gut-derived organs, including the liver in embryonic mice. Findings indicate that the FGF signaling pathway is necessary for the formation of the heart and that the FGF growth factors produced by the heart are also necessary for the induction of the foregut endoderm into the liver.

Development of the exocrine pancreas requires FGFs and FGFR2IIIb (Miralles et al., 1999). Pancreatic explants from embryonic day 11.5 rat embryos consisting of epithelium and mesenchyme showed a two fold decrease in size when treated with antisense FGFR2IIIb oligonucleotides (Miralles et al., 1999).

Finally, Arman et al. (1998) mutated the FGFR2 gene and found that homozygous mutant mouse embryos died hours after implantation. In culture, mutants formed a layer of trophoblast cells but did not maintain the inner cell mass nor produce visceral endoderm. These studies showed that FGFR2 was necessary for the outgrowth, differentiation and maintenance of the inner cell mass. Additional studies involving mammalian embryonic development showed that FGF4 was expressed in early cleavage (Rappolee et al., 1994) (Arman et al., 1999) and continued through the blastocyst, egg cylinder, and primitive streak stages (Arman et al., 1999; Niswander and Martin, 1992). After implantation the main axes of the body form as well as the extraembryonic tissue precursors (Arman et al., 1999; Gardner, 1983) and one of the earliest acting receptors in embryonic pattern formation may be FGFR2 (Arman et al., 1999; Orr-Urtreger et al., 1991).

Based on the localization of FGFRs in various embryonic tissues including the heart, liver, skin, developing nervous system, and extraembryonic membranes and the localization of hnRNP A1 protein in the same organs and tissues of the embryonic chicken, it may be hypothesized that hnRNP A1 plays a role in regulating the splice choice variants of FGFR2, and perhaps the other FGF receptors. If hnRNP A1 plays this role it would constitute a major coordinator of post-transcriptional cell type diversification during development. Certainly other targets of hnRNP A1 activity will come to light in the next few years, as well as information on the developmental roles of other nonconstitutive splice choice factors such as hnRNP A2/B1 and D classes.

EXAMPLE 3

Previous work has shown that exon 8 of FGFR2 contains a splicing silencer that interacts with the splicing factor hnRNP A1 (Del Gatto-Konczak F, Olive M, Gesnel M C, Breathnach R, 1999). The introduction of mimics (competitive antagonists) of endogenous splicing silencers can alter splicing pathways and bring about cell and tissue phenotypes characteristic of the altered pathway.

Leg bud mesenchyme cells grown in culture normally form an array of separate cartilage nodules, where each nodule is the approximate size of the cartilage primordia that lead to isolated skeletal elements during development (Downie S A, Newman S A. Morphogenetic differences between fore and hind limb precartilage mesenchyme: relation to mechanisms of skeletal pattern formation. Dev Biol 1994; 162:195-208; Downie S A, Newman S A. Different roles for fibronectin in the generation of fore and hind limb precartilage condensations. Dev Biol 1995; 172:519-30).

Figure 3:
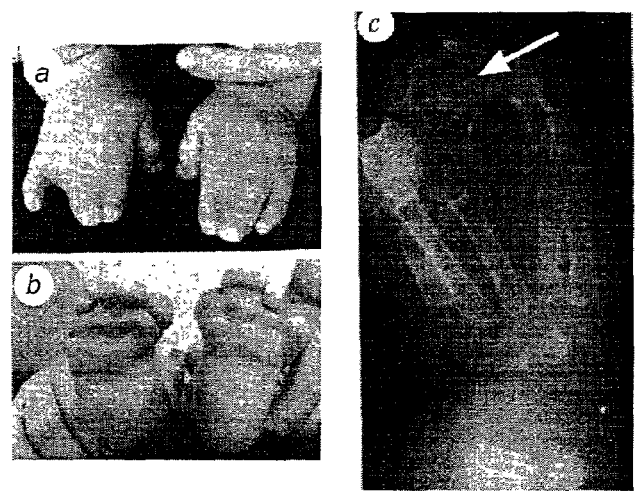
FIGS. 3a, b, and c are photographs and x-rays illustrating syndactyly of hand and feet.

FIG. 3 illustrates how Apert syndrome is caused by mutations in FGF receptor 2 (FGFR2) and leads to severe syndactyly of hands (a) and feet (b). This is seen in an X-ray as a bony bridge between the fingers where there is usually open space (c). Panels (a) and (b) are from Park W J, Theda C, Maestri N E, et al. Analysis of phenotypic features and FGFR2 mutations in Apert syndrome. Am J Hum Genet 1995; 57:321-8. (1995); panel (c) is from Wilkie A O, Slaney S F, Oldridge M, et al. Apert syndrome results from localized mutations of FGFR2 and is allelic with Crouzon syndrome. Nat Genet 1995; 9:165-72. (1995).

Figure 4:
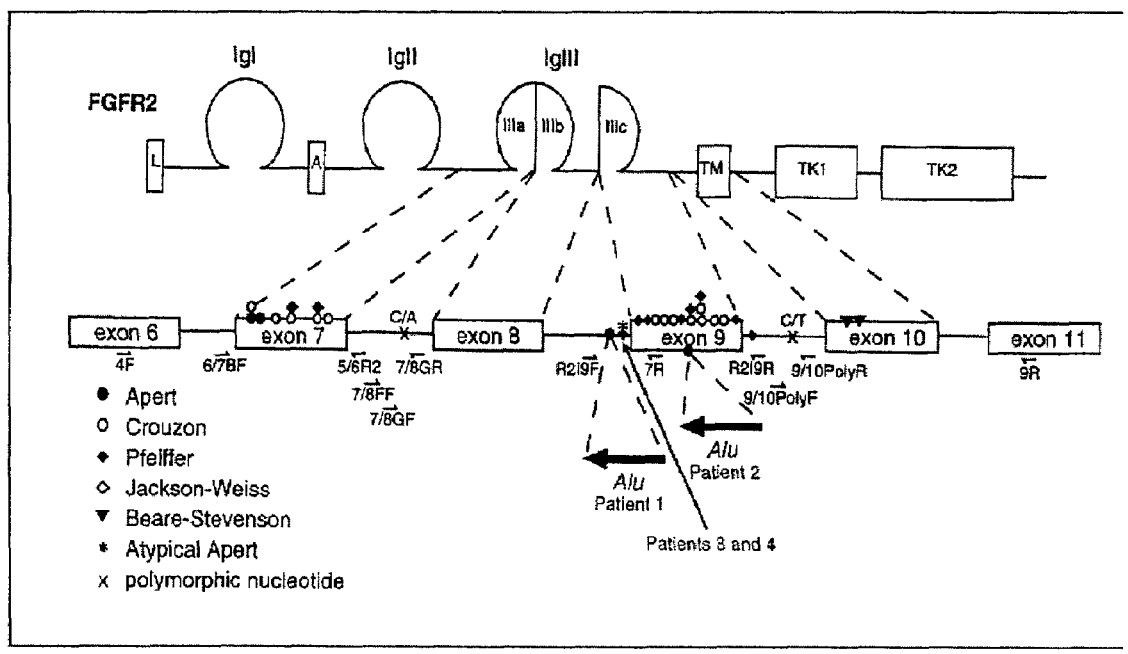
FIG. 4 is a schematic representation of the FGFR2 genetic map.

FIG. 4 illustrates that some of the most severe forms of syndactyly are seen in mutations in which FGFR2 is misspliced (patients 1 and 2) leading to the inclusion of exon 8, which specifies protein domain Ig IIIb, in the final mRNA instead of exon 9, which specifies protein domain Ig IIIc (diagram from Oldridge M, Zackai E H, McDonald-McGinn D M, et al. De novo alu-element insertions in FGFR2 identify a distinct pathological basis for Apert syndrome. Am J Hum Genet 1999; 64:446-61.). The form containing Ig IIIc is the normal one for the mesenchymal cells that form the limb skeleton during development (Orr-Urtreger A, Bedford M T, Burakova T, et al. Developmental localization of the splicing alternatives of fibroblast growth factor receptor-2 (FGFR2). Dev Biol 1993; 158:475-86).

FIG. 5a illustrates that chicken leg bud mesenchymal cells were transfected with FGFR2 exon 9 sense strand RNA (left) and exon 8 sense strand RNA (right) and grown in vitro for 6 days until cartilage was evident (blue stain). (Exons 8 and 9 are 138 and 141 bases in length, respectively, and contain no 5' translation initiation sites). As predicted by the invention disclosure, exon 8, which contains the hnRNP A1 binding site, led to a phenotype analogous to that seen in Apert syndrome, in which the skeletal elements are fused and joined, rather than separate. Transfection with the control RNA, exon 9, which does not bind to hnRNP A1, left the nodules isolated from one another, as in untransfected cultures.

FIG. 5b illustrates that a developing chicken wing was transfected with FGFR2 exon 8. In this case there was a thickening of the humerus (arrow) and appearance of developing skeletal tissue between the radius and ulna (arrowhead), again similar to Apert syndrome in which ectopic bone forms as a result of the missplicing of FGFR2.

FIG. 5c illustrates that a Northern blot was performed using poly A RNA from leg bud mesenchyme that had been transfected with FGFR2 exon 8 or exon 9 sense strand RNA. Non-transfected cells (N) produced an RNA corresponding to the molecular size of FGFR2 mRNA (arrowhead) that was detected by a radioactive exon 9-specific probe (lane 1), but was not detected by an exon 8-specific probe (lane 2). In contrast, cells transfected with exon 8 RNA (E8) produced an RNA of the correct molecular weight that was detected by the exon 8-specific probe, marking it as abnormally spliced (as suggested by the Apert-like phenotypes of the exon 8-transfected cells and limb in FIGS. 5a and 5b). Cells transfected with exon 9 (E9) produced no abnormally-spliced FGFR2 RNA containing exon 8.

It will be apparent to those skilled in the art that various modifications and variations can be made in the construction, configuration, and/or operation of the present invention without departing from the scope or spirit of the invention. For example, in the embodiments mentioned above, various changes may be made to the polynucleotide sequence and methods without departing from the scope and spirit of the invention. Further, it may be appropriate to make additional modifications or changes to the length and/or structure of the polynucleotide sequences without departing from the scope of the invention. Thus, it is intended that the present invention cover the modifications and variations of the invention provided they come within the scope of the appended claims and their equivalents.

We claim:

1. A method of modifying an activity of at least one human or avian hnRNP A protein within at least one cell, which comprises the steps of:
   introducing into the cell a plurality of RNA polynucleotide sequences comprising FGFR2 exon 8 sequences capable of binding to the hnRNP A protein; and
   interacting the RNA polynucleotide sequences with the hnRNP A protein within the cell, wherein the RNA polynucleotide sequences compete with at least one endogenous RNA sequence for interacting with the hnRNP A protein.

2. The method of claim 1, wherein the polynucleotide sequences are introduced into the cell by electroporation.

3. The method of claim 1, wherein the polynucleotide sequences are introduced into the cell by applying the polynucleotide sequences to a surface of the cell.

4. The method of claim 3, wherein the polynucleotide sequences are packaged in at least one liposome.

5. The method of claim 3, wherein the polynucleotide sequences are applied to a surface of the cell along with a detergent.

6. The method of claim 1, wherein the cell is at least one tissue culture cell.

7. The method of claim 1, wherein the cell is at least one avian cell.

8. The method of claim 1, wherein the cell is at least one non-human tissue culture cell.

9. The method of claim 1, wherein the polynucleotide sequences further comprise at least one isolated and purified RNA molecule.

10. The method of claim 1, wherein the polynucleotide sequences further comprise at least one synthetic RNA molecule.

11. The method of claim 1, wherein the polynucleotide sequences further comprise at least one synthetic RNA analog.

12. The method of claim 1, wherein the polynucleotide sequences are single-stranded.

13. The method of claim 1, wherein the step of interacting the polynucleotide sequences to the hnRNP A protein further comprises regulating the activity of the hnRNP A protein.

14. The method of claim 1, further comprising the step of determining an effect on RNA processing by monitoring at least one resulting phenotypic characteristic selected from the group consisting of abnormal skin, cell, tissue, organ, vertebral body, neural tissue, skeletal, and limb development.

15. A method of modifying an activity of at least one human or avian hnRNP A1 protein within at least one cell comprising the steps of:
   introducing into the cell a plurality of RNA polynucleotide sequences comprising FGFR2 exon 8 sequences capable of binding to the hnRNP A1 protein; and
   interacting the RNA polynucleotide sequences with the hnRNP A1 protein within the cell, wherein the RNA polynucleotide sequences compete with at least one endogenous RNA sequence for interacting with the hnRNP A1 protein.

16. The method of claim 15, further comprising the step of determining an effect on RNA processing by monitoring at least one resulting phenotypic characteristic selected from the group consisting of abnormal skin, cell, tissue, organ, vertebral body, neural tissue, skeletal, and limb development.

17. The method of claim 1, wherein the hnRNP A protein is selected from the group consisting of hnRNP A1 protein, hnRNP A1$^B$ protein, and hnRNP A2 protein.

18. A method of modifying an activity of at least one human or avian hnRNP A protein within at least one cell, which comprises the steps of:
   introducing into the cell a plurality of RNA polynucleotide sequences comprising at least one intronic splicing silencer, wherein the polynucleotide sequences are isolated and purified RNA molecules, synthetic RNA molecules, or synthetic RNA analogs;
   interacting the RNA polynucleotide sequences with the hnRNP A protein within the cell, wherein the RNA polynucleotide sequences compete with at least one endogenous RNA sequence for interacting with the hnRNP A protein; and
   altering the splicing of the at least one endogenous RNA sequence.

19. The method of claim 18, wherein the hnRNP A protein is selected from the group consisting of hnRNP A1 protein, hnRNP A1$^B$ protein, and hnRNP A2 protein.

20. A method of modifying an activity of at least one human or avian hnRNP A protein within at least one cell, comprising the steps of:
   introducing into the cell a plurality of RNA polynucleotide sequences comprising at least one intronic splicing enhancer; and
   interacting the RNA polynucleotide sequences with the hnRNP A protein within the cell, wherein the RNA polynucleotide sequences compete with at least one endogenous RNA sequence for interacting with the hnRNP A protein.

21. The method of claim 20, wherein the hnRNP A protein is selected from the group consisting of hnRNP A1 protein, hnRNP A1$^B$ protein, and hnRNP A2 protein.

22. A method of modifying an activity of at least one human or avian hnRNP A protein within at least one cell, which comprises the steps of:
   introducing into the cell a plurality of RNA polynucleotide sequences comprising at least one exonic splicing silencer, wherein the polynucleotide sequences are isolated and purified RNA molecules, synthetic RNA molecules, or synthetic RNA analogs;
   interacting the RNA polynucleotide sequences with the hnRNP A protein within the cell, wherein the RNA polynucleotide sequences compete with at least one endogenous RNA sequence for interacting with the hnRNP A protein; and
   altering the splicing of the at least one endogenous RNA sequence.

23. The method of claim 22, wherein the hnRNP A protein is selected from the group consisting of hnRNP A1 protein, hnRNP A1$^B$ protein, and hnRNP A2 protein.

24. A method of modifying an activity of at least one human or avian hnRNP A protein within at least one cell, which comprises the steps of:
   introducing into the cell a plurality of RNA polynucleotide sequences comprising at least one exonic splicing enhancer, wherein the polynucleotide sequences are isolated and purified RNA molecules, synthetic RNA molecules, or synthetic RNA analogs;
   interacting the RNA polynucleotide sequences with the hnRNP A protein within the cell, wherein the RNA polynucleotide sequences compete with at least one endogenous RNA sequence for interacting with the hnRNP A protein; and
   altering the splicing of the at least one endogenous RNA sequence.

25. The method of claim 24, wherein the hnRNP A protein is selected from the group consisting of hnRNP A1 protein, hnRNP A1$^B$ protein, and hnRNP A2 protein.

* * * * *

```
                        SEQUENCE LISTING

<160> NUMBER OF SEQ ID NOS: 10

<210> SEQ ID NO 1
<211> LENGTH: 1689
<212> TYPE: DNA
<213> ORGANISM: Gallus gallus
<220> FEATURE:
<221> NAME/KEY: Misc_Feature
<222> LOCATION: (1)..(1689)
<223> OTHER INFORMATION: Full length cDNA sequence of Gallus gallus
      hnRNP A1.
<220> FEATURE:
<221> NAME/KEY: Misc_Feature
<222> LOCATION: (141)..(1276)
<223> OTHER INFORMATION: Open reading frame of cDNA sequence from Gallus
      gallus hnRNP A1.

<400> SEQUENCE: 1
gcgtctccac ccctcagcgg gcggcggtga gtgcgccagg ccagcgccgg cgtgggaccg      60
agcgggcgtg aaggcgcgag ctgaacgctg gcacggtttc ctagatctaa aagaaaggcc     120
gagttagagt acccttccaa aatggctgct attaaggaag agagagaggt ggaagattac     180
aagagaaaaa ggaagacgat cagcacaggc catgagccta aggagccaga gcagttgaga     240
aagctgttca ttggaggtct gagcttcgag acgacggatg atagcttgag agagcacttt     300
gaaaaatggg gcacactcac ggactgtgtg gtgatgagag acccacaaac aaaacgttcc     360
agaggctttg gctttgttac ttactcttgc gtggaagagg tggatgcggc catgagcgct     420
cgaccacata aggtggatgg acgtgtggtt gaaccaaaga gagcagtttc aagggaggat     480
tctgtaaagc ctggggcgca tctcacagta aagaaaatat ttgttggtgg cattaaagaa     540
```

-continued

```
gatacagaag aatataattt aagggggtac tttgaaacat atggcaagat cgaaacgata      600
gaagtcatgg aagacagaca aagtggaaag aaaagaggct tcgcttttgt aacttttgat      660
gatcacgata cagttgataa aattgttgtt cagaaatacc atactataaa tggtcataac      720
tgcgaagata aaaaagcact ctcaaaacaa gagatgcaga ctgccagctc tcagagaggt      780
cgtgggggtg gttcaggcaa cttcatgggt cgtggaaatt ttggaggtgg tggaggaaac      840
tttggccgag gaggaaactt tggtggaaga ggaggctatg gtggtggtgg cggtggtggg      900
agcagaggaa gctttggggg tggtgatgga tacaacggat tggtgatgg tggcaactat       960 ggaggtggtc ctggctatgg cagcagaggg ggttatggtg gtggtggagg accaggatat     1020
ggaaacccag gtggtggata tggaggtgga ggaggaggat atggtggcta caatgaagga     1080
ggcaattttg gaggtggtaa ttatggaggc agtggaaact acaatgactt tggtaactac     1140
agtggacagc agcagtccaa ttacggtccc atgaaggtg gtgcagtttt ggtggtaga      1200 agttcaggca gtccctatgg tggtggttat ggatctggaa gtggaagtgg gggctatggt     1260
ggtagaagat tctaaaaatg ctaccagaaa aagggctaca gttcttagca ggagagagag     1320
cgaggagttg tcaggaaagc tgcagtttac tttgagacag tcgtcccaaa tgcattagag     1380
gaactgtaaa atctgccaca gaaggaacga tgatccatag tcagaaaagt tactgcagct     1440
taaacaggaa accttcttg ttcaggactg tcatagccac agtttgcaaa agagcagct      1500 attggttaat gcaatgtagt gtcgttagat gtacatcctg aggtctttat ctgttgtagc     1560
tttgtctttc tttttctttt ttattttccc attacatcag gtatattgcc ctgtaaattg     1620
tggtagtggt acaaggaata aacaaattaa ggaattttg gcttttcaaa aaaaaaaaa      1680 aaaaaaaaa                                                            1689
```

<210> SEQ ID NO 2
<211> LENGTH: 378
<212> TYPE: PRT
<213> ORGANISM: Gallus gallus
<220> FEATURE:
<221> NAME/KEY: PEPTIDE
<222> LOCATION: (1)..(378)
<223> OTHER INFORMATION: Amino acid sequence of chicken hnRNP A1.

<400> SEQUENCE: 2

```
Met Ala Ala Ile Leu Gly Gly Ala Gly Val Gly Ala Thr Leu Ala Leu
1               5                   10                  15

Ala Leu Thr Ile Ser Thr Gly His Gly Pro Leu Gly Pro Gly Gly Leu
            20                  25                  30

Ala Leu Leu Pro Ile Gly Gly Leu Ser Pro Gly Thr Thr Ala Ala Ser
        35                  40                  45

Leu Ala Gly Gly Pro Gly Leu Thr Gly Thr Leu Thr Ala Cys Val Val
    50                  55                  60

Met Ala Ala Pro Gly Thr Leu Ser Ala Gly Pro Gly Pro Val Thr
65                  70                  75                  80

Thr Ala Thr Val Gly Gly Val Ala Ala Ala Met Ser Ala Ala Pro His
                85                  90                  95

Leu Val Ala Gly Ala Val Val Gly Pro Leu Ala Ala Val Ser Ala Gly
            100                 105                 110

Ala Ser Val Leu Pro Gly Ala His Leu Thr Val Leu Leu Ile Pro Val
        115                 120                 125

Gly Gly Ile Leu Gly Ala Thr Gly Gly Thr Ala Leu Ala Gly Thr Pro
    130                 135                 140
```

```
Gly Thr Thr Gly Leu Ile Gly Thr Ile Gly Val Met Gly Ala Ala Gly
145                 150                 155                 160

Ser Gly Leu Leu Ala Gly Pro Ala Pro Val Thr Pro Ala Ala His Ala
            165                 170                 175

Thr Val Ala Leu Ile Val Val Gly Leu Thr His Thr Ile Ala Gly His
        180                 185                 190

Ala Cys Gly Ala Leu Leu Ala Leu Ser Leu Gly Gly Met Gly Thr Ala
    195                 200                 205

Ser Ser Gly Ala Gly Ala Gly Gly Ser Gly Ala Pro Met Gly Ala
    210                 215                 220

Gly Ala Pro Gly Gly Gly Gly Ala Pro Gly Ala Gly Ala Pro
225                 230                 235                 240

Gly Gly Ala Gly Gly Thr Gly Gly Gly Gly Gly Gly Ser Ala
            245                 250                 255

Gly Ser Pro Gly Gly Gly Ala Gly Thr Ala Gly Pro Gly Ala Gly Gly
            260                 265                 270

Ala Thr Gly Gly Gly Pro Gly Thr Gly Ser Ala Gly Gly Thr Gly Gly
        275                 280                 285

Gly Gly Gly Pro Gly Thr Gly Ala Pro Gly Gly Thr Gly Gly
            290                 295                 300

Gly Gly Gly Thr Gly Gly Thr Ala Gly Gly Ala Pro Gly Gly Gly
305                 310                 315                 320

Ala Thr Gly Gly Ser Gly Ala Thr Ala Ala Pro Gly Ala Thr Ser Gly
            325                 330                 335

Gly Gly Gly Ser Ala Thr Gly Pro Met Leu Gly Gly Ser Pro Gly
            340                 345                 350

Gly Ala Ser Ser Gly Ser Pro Thr Gly Gly Gly Thr Gly Ser Gly Ser
        355                 360                 365

Gly Ser Gly Gly Thr Gly Gly Ala Ala Pro
    370                 375

<210> SEQ ID NO 3
<211> LENGTH: 320
<212> TYPE: PRT
<213> ORGANISM: Homo sapiens
<220> FEATURE:
<221> NAME/KEY: PEPTIDE
<222> LOCATION: (1)..(320)
<223> OTHER INFORMATION: Amino acid sequence of human hnRNP A1.

<400> SEQUENCE: 3

Met Ser Lys Ser Glu Ser Pro Lys Glu Pro Glu Gln Leu Arg Lys Leu
1               5                   10                  15

Phe Ile Gly Gly Leu Ser Phe Glu Thr Thr Asp Glu Ser Leu Arg Ser
            20                  25                  30

His Phe Glu Gln Thr Gly Thr Leu Thr Asp Cys Val Val Met Arg Asp
        35                  40                  45

Pro Asn Thr Lys Arg Ser Arg Gly Phe Gly Phe Val Thr Tyr Ala Thr
    50                  55                  60

Val Glu Glu Val Asp Ala Ala Met Asn Ala Arg Pro His Lys Val Asp
65                  70                  75                  80

Gly Arg Val Val Glu Pro Lys Arg Ala Val Ser Arg Glu Asp Ser Gln
                85                  90                  95

Arg Pro Gly Ala His Leu Thr Val Lys Lys Ile Phe Val Gly Gly Ile
            100                 105                 110

Lys Glu Asp Thr Glu Glu His His Leu Arg Asp Tyr Phe Glu Gln Tyr
```

```
                  115                 120                 125
Gly Lys Ile Glu Val Ile Glu Ile Met Thr Asp Arg Gly Ser Gly Lys
    130                 135                 140

Lys Ala Gly Phe Ala Phe Val Thr Phe Asp Asp His Asp Ser Val Asp
145                 150                 155                 160

Lys Ile Val Ile Gln Lys Tyr His Thr Val Asn Gly His Asn Cys Glu
                165                 170                 175

Val Arg Lys Ala Leu Ser Lys Gly Glu Met Ala Ser Ala Ser Ser Ser
            180                 185                 190

Gln Arg Gly Arg Ser Gly Ser Gly Ala Phe Gly Gly Arg Gly Gly
        195                 200                 205

Gly Phe Gly Gly Asn Asp Asn Phe Gly Arg Gly Gly Asn Phe Ser Gly
    210                 215                 220

Arg Gly Gly Phe Gly Gly Ser Arg Gly Gly Gly Tyr Gly Gly Ser
225                 230                 235                 240

Gly Asp Gly Tyr Asn Gly Phe Gly Asn Ala Gly Ser Asn Phe Gly Gly
                245                 250                 255

Gly Gly Ser Tyr Asn Asp Phe Gly Asn Tyr Asn Asn Gln Ser Ser Asn
            260                 265                 270

Phe Gly Pro Met Lys Gly Gly Asn Phe Gly Gly Arg Ser Ser Gly Pro
        275                 280                 285

Tyr Gly Gly Gly Gly Gln Tyr Pro Ala Lys Pro Arg Asn Gln Gly Gly
    290                 295                 300

Tyr Gly Gly Ser Ser Ser Ser Ser Tyr Gly Ser Gly Arg Arg Pro
305                 310                 315                 320

<210> SEQ ID NO 4
<211> LENGTH: 1136
<212> TYPE: DNA
<213> ORGANISM: Gallus gallus
<220> FEATURE:
<221> NAME/KEY: Misc_Feature
<222> LOCATION: (1)..(1136)
<223> OTHER INFORMATION: Open reading frame of cDNA for chicken hnRNP
      A1.

<400> SEQUENCE: 4
aatggctgct attaaggaag agagagaggt ggaagattac aagagaaaaa ggaagacgat      60
cagcacaggc catgagccta aggagccaga gcagttgaga aagctgttca ttggaggtct     120
gagcttcgag acgacggatg atagcttgag agagcacttt gaaaaatggg cacactcac     180 ggactgtgtg gtgatgagag acccacaaac aaaacgttcc agaggctttg ctttgttac     240 ttactcttgc gtggaagagg tggatgcggc catgagcgct cgaccacata aggtggatgg     300
acgtgtggtt gaaccaaaga gagcagtttc aagggaggat tctgtaaagc ctggggcgca     360
tctcacagta aagaaaatat tgttggtgg cattaaagaa gatacagaag aatataattt     420 aaggggtac tttgaaacat atggcaagat cgaaacgata gaagtcatgg aagacagaca     480
aagtggaaag aaaagaggct cgcttttgt aactttgat gatcacgata cagttgataa     540
aattgttgtt cagaaatacc atactataaa tggtcataac tgcgaagata aaaaagcact     600
ctcaaaacaa gagatgcaga ctgccagctc tcagagaggt cgtgggggtg gttcaggcaa     660
cttcatgggt cgtggaaatt ttggaggtgg tggaggaaac tttggccgag aggaaacttt     720
tggtggaaga ggaggctatg ggggtggtgg tggcggtggt gggagcagag gaagctttgg     780
gggtggtgat ggatacaacg gatttggtga tggtggcaac tatggaggtg gtcctggcta     840
```

-continued

```
tggcagcaga gggggttatg gtggtggtgg aggaccagga tatggaaacc caggtggtgg      900
atatggaggt ggaggaggag gatatggtgg ctacaatgaa ggaggcaatt ttggaggtgg      960
taattatgga ggcagtggaa actacaatga ctttggtaac tacagtggac agcagcagtc     1020
caattacggt cccatgaaag gtggtggcag ttttggtggt agaagttcag gcagtcccta     1080
tggtggtggt tatggatctg gaagtggaag tggggctat ggtggtagaa gattct          1136
```

<210> SEQ ID NO 5
<211> LENGTH: 10
<212> TYPE: RNA
<213> ORGANISM: Homo sapiens
<220> FEATURE:
<221> NAME/KEY: Misc_Feature
<222> LOCATION: (1)..(10)
<223> OTHER INFORMATION: Exonic splice silencer (ESS) nucleic acid
      sequence for hnRN A1.

<400> SEQUENCE: 5
uagggcaggc                                                              10

<210> SEQ ID NO 6
<211> LENGTH: 10
<212> TYPE: RNA
<213> ORGANISM: Gallus gallus
<220> FEATURE:
<221> NAME/KEY: Misc_Feature
<222> LOCATION: (1)..(10)
<223> OTHER INFORMATION: Exonic splice silencer (ESS) nucleic acid
      sequence for hnRNP A1.

<400> SEQUENCE: 6
uagggagggc                                                              10

<210> SEQ ID NO 7
<211> LENGTH: 8
<212> TYPE: PRT
<213> ORGANISM: Homo sapiens
<220> FEATURE:
<221> NAME/KEY: SITE
<222> LOCATION: (1)..(1)
<223> OTHER INFORMATION: Xaa represents a Lysine or an Arginine
<220> FEATURE:
<221> NAME/KEY: SITE
<222> LOCATION: (3)..(3)
<223> OTHER INFORMATION: Xaa represents a phenylalanine or tyrosine.
<220> FEATURE:
<221> NAME/KEY: SITE
<222> LOCATION: (4)..(4)
<223> OTHER INFORMATION: Xaa represents a glycine or alanine.
<220> FEATURE:
<221> NAME/KEY: Misc_Feature
<222> LOCATION: (7)..(7)
<223> OTHER INFORMATION: Xaa can be any naturally ocurring amino acid.
<220> FEATURE:
<221> NAME/KEY: SITE
<222> LOCATION: (8)..(8)
<223> OTHER INFORMATION: Xaa represents a phenylalanine or tyrosine.

<400> SEQUENCE: 7

Xaa Gly Xaa Xaa Pro Val Xaa Xaa
1               5

<210> SEQ ID NO 8
<211> LENGTH: 148
<212> TYPE: PRT
<213> ORGANISM: Homo sapiens
<220> FEATURE:
<221> NAME/KEY: Misc_Feature
<222> LOCATION: (1)..(6)

<223> OTHER INFORMATION: Correspond to amino acids 16 - 21 of hnRNP A1.
<220> FEATURE:
<221> NAME/KEY: Misc_Feature
<222> LOCATION: (7)..(39)
<223> OTHER INFORMATION: Correspond to amino acids 22 - 54 of hnRNP A1.
<220> FEATURE:
<221> NAME/KEY: Misc_Feature
<222> LOCATION: (40)..(47)
<223> OTHER INFORMATION: Correspond to amino acids 55 - 62 of hnRNP A1.
<220> FEATURE:
<221> NAME/KEY: Misc_Feature
<222> LOCATION: (48)..(91)
<223> OTHER INFORMATION: Correspond to amino acids 63 - 106 of hnRNP A1.
<220> FEATURE:
<221> NAME/KEY: Misc_Feature
<222> LOCATION: (92)..(97)
<223> OTHER INFORMATION: Correspond to amino acids 107 - 112 of hnRNP
    A1.
<220> FEATURE:
<221> NAME/KEY: Misc_Feature
<222> LOCATION: (98)..(140)
<223> OTHER INFORMATION: Correspond to amino acids 113 - 145 of hnRNP
    A1.
<220> FEATURE:
<221> NAME/KEY: Misc_Feature
<222> LOCATION: (141)..(148)
<223> OTHER INFORMATION: Correspond to amino acids 146 - 153 of hnRNP
    A1.

<400> SEQUENCE: 8

Leu Phe Ile Gly Gly Leu Ser Phe Glu Thr Thr Asp Glu Ser Leu Arg
1               5                   10                  15

Ser His Phe Glu Gln Thr Gly Thr Leu Thr Asp Cys Val Val Met Arg
            20                  25                  30

Asp Pro Asn Thr Lys Arg Ser Arg Gly Phe Gly Pro Val Thr Tyr Ala
        35                  40                  45

Thr Val Glu Glu Val Asp Ala Ala Met Asn Ala Arg Pro His Lys Val
    50                  55                  60

Asp Gly Arg Val Val Glu Pro Lys Arg Ala Val Ser Arg Glu Asp Ser
65                  70                  75                  80

Gln Arg Pro Gly Ala His Leu Thr Val Lys Lys Ile Phe Val Gly Gly
                85                  90                  95

Ile Thr Val Lys Lys Ile Phe Val Gly Gly Ile Lys Glu Asp Thr Glu
            100                 105                 110

Glu His His Leu Arg Asp Tyr Phe Glu Gln Tyr Gly Lys Ile Glu Val
        115                 120                 125

Ile Glu Ile Met Thr Asp Arg Gly Ser Gly Lys Lys Arg Gly Phe Ala
    130                 135                 140

Phe Val Thr Phe
145

<210> SEQ ID NO 9
<211> LENGTH: 28
<212> TYPE: PRT
<213> ORGANISM: Homo sapiens
<220> FEATURE:
<221> NAME/KEY: Misc_Feature
<222> LOCATION: (1)..(28)
<223> OTHER INFORMATION: hnRNP A2 is defined as human hnRNP core
    protein.
<220> FEATURE:
<221> NAME/KEY: Misc_Feature
<222> LOCATION: (1)..(28)
<223> OTHER INFORMATION: OTHER: Max number of positions shown; some may
    be missing.
<220> FEATURE:
<221> NAME/KEY: Misc_Feature
<222> LOCATION: (1)..(6)

-continued

```
<223> OTHER INFORMATION: Correspond to amino acids 11 - 16 of hnRNP A2.
<220> FEATURE:
<221> NAME/KEY: Misc_Feature
<222> LOCATION: (7)..(14)
<223> OTHER INFORMATION: Correspond to amino acids 50 - 57 of hnRNP A2.
<220> FEATURE:
<221> NAME/KEY: Misc_Feature
<222> LOCATION: (15)..(20)
<223> OTHER INFORMATION: Correspond to amino acids 102 - 107 of hnRNP
      A2.
<220> FEATURE:
<221> NAME/KEY: Misc_Feature
<222> LOCATION: (21)..(28)
<223> OTHER INFORMATION: Correspond to amino acids 141 - 148 of hnRNP
      A2.

<400> SEQUENCE: 9

Leu Phe Ile Gly Gly Leu Ala Gly Phe Gly Pro Val Thr Phe Leu Phe
1               5                   10                  15

Val Gly Gly Ile Arg Gly Phe Gly Phe Val Thr Phe
            20                  25

<210> SEQ ID NO 10
<211> LENGTH: 12
<212> TYPE: PRT
<213> ORGANISM: Homo sapiens
<220> FEATURE:
<221> NAME/KEY: Misc_Feature
<222> LOCATION: (1)..(12)
<223> OTHER INFORMATION: hnRNP is defined as a human hnRNP core protein.
<220> FEATURE:
<221> NAME/KEY: Misc_Feature
<222> LOCATION: (1)..(12)
<223> OTHER INFORMATION: Correspond to amino acids 3 - 14 of hnRNP B2.

<400> SEQUENCE: 10

Lys Thr Leu Glu Thr Val Pro Leu Glu Arg Lys Lys
1               5                   10
```